ns**

United States Patent [19]

Shibano et al.

[11] Patent Number: 5,292,643
[45] Date of Patent: Mar. 8, 1994

[54] FUSARIC ACID RESISTANT GENES

[75] Inventors: Yuji Shibano, Toyonaka; Hideyoshi Toyoda, Hirakata; Ryutaro Utsumi, Nara; Kazuaki Obata, Toyonaka, all of Japan

[73] Assignees: Suntory Limited; Daikin Industries, Ltd., both of Osaka, Japan

[21] Appl. No.: 661,610

[22] Filed: Feb. 28, 1991

[30] Foreign Application Priority Data

Feb. 28, 1990 [JP] Japan .................................. 2-45481
Feb. 18, 1991 [JP] Japan ................................. 3-044027

[51] Int. Cl.$^5$ ...................... C12N 15/00; C12N 15/11; C12N 15/31; C12N 15/70
[52] U.S. Cl. ........................... 435/69.1; 435/252.33; 435/320.1; 435/852; 435/874; 536/23.7
[58] Field of Search .............. 435/69.1, 172.1, 172.3, 435/252.33, 252.4, 253.3, 320.1, 852, 874; 536/27, 23.2, 23.1, 23.7; 530/350; 424/93 D

[56] References Cited

U.S. PATENT DOCUMENTS 4,988,586  1/1991  Toyoda ........................... 424/93 D
5,178,863  1/1993  Toyoda ........................... 424/93 D

FOREIGN PATENT DOCUMENTS 0251320  1/1988  European Pat. Off. .
0255774  2/1988  European Pat. Off. .
0257756  3/1988  European Pat. Off. .
198974  of 1988  Japan .
22957   of 1990  Japan .

OTHER PUBLICATIONS

Patent Abstracts of Japan, vol. 12, No. 482 (C-553)(3329), Dec. 15, 1988, & JP-A-63-198607, Aug. 17, 1988, H. Toyoda, et al., "Method for Controlling Fusarium Blight".

J. Cell. Biochem. Supplement 15A, p. 46, 1991, S. Ouchi, et al., "Microbial Genes for Fusaric Acid Degradation and Their Use for the Production of Disease Resistant Plants".

Ryutaro Utsumi et al, Cloning of Fusaric Acid–Detoxifying Gene from Cladosporium Wernekii; A New Strategy for the Prevention of Plant Diseases, 6090 Journal of Biotechnology 8 (1988), Oct., No. 4, pp. 311–315, Amsterdam, The Netherlands.

S. E. Lindow et al., Genetic Engineering of Bacteria from Managed and Natural Habitats, 896 Science, vol. 244, pp. 1300–1307, Jun. 16, 1989, Washington, D.C.

David L. J. Quicke et al, Extended Summaries Pesticides Group and Physicochemical and Biophysical Panel Symposium Novel Approaches in Agrochemical Research, 2411 Pesticide Science, 20 (1987) No. 4, Barking, Essex, Great Brtain, pp. 315–320.

Brian Fristensky, cDNA Sequences for Pea Disease Resistance Response Genes, Plant Molecular Biology 11: 713–715 (1988).

*Primary Examiner*—Robert A. Wax
*Assistant Examiner*—Dian C. Jacobson
*Attorney, Agent, or Firm*—Oblon, Spivak, McClelland, Maier & Neustadt

[57] ABSTRACT

Fusaric acid resistant genes derived from fusaric acid decomposing or detoxifying microorganisms such as *Pseudomonas cepacia* and *Klebsiella oxytoca* are described. Also described are DNA fragments and plasmids, which comprise such fusaric acid resistant genes. Host cells comprising such plasmids are also described.

11 Claims, 15 Drawing Sheets

FIG. 4(1)

```
  1 GAATTCATCTGCTGGGCGGCCCGGGTAAAGCTTCCCGCGTCGACCACGCGGACGAATACCCGCATGTTTGTAACGTATCCATCCATTACCGTTTGAA   100
101 TCCGGACGGATTGTTGCACAGAGGCAAACAAGTATTGTCTCAGGATTCGTAAAAATGACTTGCACCCTGTGTCCATATATTCAGGAATCGCTGAAAAATAT  200
201 AATCGCATCGACTCATCTATATCCGAAAGGAGAAAAATCGTGCAGTCTCCGGCGACAAAAGGGACGCTCGCACTGGGCGGTTCTTGCAGTCTCATTAATA  300
301 ATGGCCGGGTGCGCGGAGCATGGGCGACAACAAGCCAGTCGGGCCCGCATCGAAGGAACGCGCTCGATGCCGGCGGCCATCCGGCGGCCGGCCGACCGCG  400
401 ACGGGGCTGGCCCGCCGGACTGGTGCGCGCCGACTGGTGCGCGCCGGCGCCGCAGGCCGGCAACCCGACGCTCGGGC  500
                                                                                fadA
501 CGCCGAGGCGCTGCGCGAAGCGCAGGCGATGGCGGCGGTGGCCGCGCTCGGCCGCGATCCGCAACTCTCGCTGATGGCCAGCACT  600
  1                                 MetAlaArgValAlaArgSerAlaAlaArgValAlaAlaArgValMetLeuArgGlnHisT   24
601 GGCCGGACAACGTCTATTACGGCCCCGGCCCGCTCGCGAACACCGACACACCTGGAACAACACCGGCAGCGCTGCTGCCTACCACCTCGACCTGTGGG   700
 24 rpProAspAsnValIleTyrTyrGlyProGlyProLeuAlaAsnThrAspThrTrpAsnAsnThrGlyThrLeuGlyLeuSerTyrHisLeuAspLeuTrpGl   57
701 CAAGGACAAGAAGAACGCGACGAGCGCGCGCTCGATACCGGCTCGATAACCGGCTCGATACCGGAAGCTCGAAGCTCAACGTCGTGCGC  800
 57 yLysAspLysAsnAlaThrGluArgAlaLeuAspThrAlaHisAlaThrAlaAlaLysLeuLeuGlyValAlaLysValAlaArg   90
801 GCGTACGTCGGCATGTCGATGAACTACGCGCTGCTCCTCGACCTCGCGCGCACGAAAGTTCGAACGCTGGAGCGGCAGCAGGCCAGGCCAAGCGGCTGC  900
 91 AlaTyrValGlyMetSerMetAsnTyrAlaLeuLeuAspLeuAlaHisGluThrPheGluArgSerLeuAlaArgLysArgLeuG   124
901 AGGCTGGCCTCGGCACGCAGCTCGAGGTGAGCCAGGCGGAATCGACGCTGCCGGACTATGAGCGGCCAGATCGAGCGGCCAGAAGGATCCAGCTCGC 1000
124 lnAlaGlyLeuGlyThrGlnLeuGluValSerGlnAlaIleSerThrLeuProAspTyrGluArgGlnIleAspSerTyrGluGluAlaIleGlnLeuAl  157
```

FIG. 4(2)

```
1001 GCGGCACCAGCTCGCCGCACTGGCCGCAAGGGCCCCGGCGATGCCGGGATCAAGGCCCTCGGTGTCGCTCGACGCACCGGCCGGCTTGCCGTCG 1100
 157  aArgHisGlnLeuAlaAlaLeuAlaGlyLysGlyProGlyAlaGlyAspAlaIleLysArgProArgLeuSerLeuAspAlaProAlaGlyLeuProSer 190

1101 GCGATGCCGGCCGACCTGTCGGCGCTGCTGGGCCTGTATCGCCGCCCCGACGTCGTCGCTGCGGCCATGCGGACGTCGACGTCGCAAAGGCTTCGT 1200
 191  AlaMetProAlaAspLeuLeuGlyArgArgProAspValValAlaAlaAlaArgTrpThrValAspAlaGlnAlaArgGlyIleAspValAlaLysAlaSerP 224

1201 TCTATCCGAACATCGACCTGCTCGCAGACGTCGGCGCTTCGGCGTGACCGCGTTCACCGACTTCCTGCGCGATGAACGGGGCTGGACGGCCGG 1300
 224  heTyrProAsnIleAspLeuLeuAlaThrValGlyValPheGlyValThrAlaProPheThrAspPheLeuArgAlaMetAsnGlyGlyTrpThrAlaGl 257

1301 CCCCGGCTGTCGCTGCCGATCTTCGAAGGCGCGGCCTCGGCGCTGCCCCAGGCGGGCTACGACCAGGCGGTCGAGCAATACAACCA 1400
 257  yProAlaLeuSerLeuProIlePheGluGlyGlyArgLeuArgLeuArgGlyArgLeuArgArgAlaGlnAlaAsnAlaGlyValArgProGlyGlyArgAlaIleGlnPro 290

1401 GACGATCGTCGGGCGCTCAAGGACATCCGCGACCAGGTCGTCGCCGCAAGGCTTCCGCGATCCGTTCGCCGCCGGATACGCAGAAGAAGGACGCCGCACGCTCGGTGGCCGCCAAC 1500
 291  AspAspArgArgArgAlaGlnAlaGlyHisArgArgProIleArgArgProGlyArgProPheAlaArgTyrAlaAlaGluGlyArgArgThrLeuGlyArgGlnA 324

1501 GACCGCAGTTACCAGTCTGCGCGAAGGCTTCCGCGCCCGGCGACTAGTCAACCTGCTGGTCGCCAGCAGCAATTGTTGGCGCACAGGAA 1600
 324  rgProGlnLeuProAlaValAlaArgArgLeuProProAspArgArgLeuArgArgGlnArgAlaGlaHisAlaGlnAlaAlaAlaIleValGlyAlaHisArgLy 357

1601 ACGGCCCGCCGATCGGAAACGCCTCGCGGCTCAACTGATGCGCGGTGCCGGGGTGCCCGAGACGGGCACGTGCCGGGCAGCCAC 1700
 357  sArgProProHisArgSerGluArgLeuArgLeuAlaGlaHisAlaGlnLeuMetAlaGlaAlaLeuGlyGlyValGluThrGlyThrAspValProGlySerGln 390

1701 TCGTCGCATGGCGAATCCGCCGGGCCGCGCCAGCCGCCGGGTGCCGAAACCCGTGCGGTAGCGCCGCCGCCGCCGCCGGCCGG 1800
 391  SerSerHisGlyGluSerAlaAlaAlaProAlaAlaAlaAlaSerGlyAlaAlaLysProAlaAlaAlaArgProAlaAlaGlnValAlaAlaAlaA 423
       fadB 1801 CCGGTGCCGCCGGTGCCGCCGCCGCACGTAACCCGGAGCGACGCCATGTCAGCTCCTCTCCCCGACCGCCGTTCGGCCCTGG 1898
 423,1 laGlyAlaAlaGlyValProAlaAlaArg***    MetSerAlaSerSerProLeuSerProThrAlaGlyProPheAlaAlaTrp 18
```

FIG. 4(3)

```
1901 TATGCCGGTTCGGCGACTGGGCCCGACCGACGGGCGCCTGCTCAAGGCACTGCTCGGGCCTTCATCGCCTCCGGCGTGTCGATGC 2000
  19 TyrAlaAlaPheGlyAspTrpAlaArgThrAspGlyAlaAlaTrpLeuTyrPheLysAlaLeuLeuAlaAlaPheIleAlaLeuGlyValSerMetA  52
2001 GGCTCGACCTGCCGGCGCCGAAAACGGGCAATGACGACGTCTTCATCGTGATGCAGCGAAAAGCGGGCCGTGCTCGCGAAAAGCTTCTACGGGTCGCC 2100
  52 rgLeuAspLeuProAlaProLysThrAlaMetThrThrValPheIleValMetGlnArgLysAlaProCysSerArgLysAlaSerThrGlySerPr  85
2101 GGCACGATCTTCGGGCTCACGCGACGTTCGTCCCGGCAGCAGTGTTCCTGCTGGCGATCGCCCTGTGGATCGCGCTGT 2200
  85 oAlaArgSerSerGlyCysSerArgSerArgSerArgSerCysSerProCysGlySerArgCys 118
2201 GCACCGGCCGGGCGCGCAACCTTCCGCAGTTACGGCTTCCTGCTCCGGGCTATACGACCGGCTGATCGGCCTGCCCGTCGCAGCACCC 2300
 119 AlaProProAlaProArgAlaThrAlaThrSerAlaValThrAlaSerCysSerProAlaIleArgProArg*** 142
                                                     fadC
2301 GGATGGGCATTCATGAGCGGATGACGCGGGTCTCCGAAGTCATCATCGGGATCGTGTCGGCCGTCGCAGCGCGCTCGTGTTTCCTCGGTACACG 2400
   1                                    MetSerAlaMetThrArgValSerGluValIleIleGlyIleValSerAlaLeuValIlePheProArgTyrThr 29
2401 GGCGAGCAGATGCGCACGACGGTGCGCAAGCGCTTCGGCCAGTCGACTACGTGGCCAGTCGTCTCGGCCTTCGACTACGTGGCCAGTCGTCTCGGGCAGTCGATCGAGA 2500
  30 GlyGluGlnMetArgThrThrValArgLysArgPheGlySerPheValAspTyrValAlaSerAlaLeuSerGlyGlnLeuAspArgAlaHisIleGluT 63
2501 CCATCCATACGCGCTTCGCGGCTTACGTGGTCGGCTTCGAGGATCCGGCAGCATGGCCGTGTTCGAGGATCCGGACACGGCAGGCCGCCTCGC 2600
  63 hrIleHisThrArgPheAlaTyrValValGlyPheGluAlaAlaValPheGluAspProAspThrArgMetArgSerGlyArgLeuAl 96
2601 GCGGCTGAACAGCGAGTTCATGAGCGGTCGAGCCGCTTTCACGCGCTGACCAGCGCACGGCTCGACGCGGCGCAGGCCGGATCGAT 2700
  96 aArgLeuAsnSerGluPheMetSerAlaSerSerArgPheHisAlaLeuHisGlnLeuMetAsnArgLeuHisAlaGlnAlaAlaGlyAlaAlaIleAsp 129
2701 GCGATCGAGCCGTATTTCCGCGAGATCGCGCTGCTCACGCGCGAGAATGGCAACGGGTGCGCACGTGATCGACGCCGACTGGCCGAGCAACTGC 2800
 130 AlaIleGluProTyrPheArgGluIleAlaProLeuLeuThrArgAsnGlyValArgThrSerIleAspAlaIleAspAlaHisSerAlaAlaGluGlnLeuL 163
```

FIG. 4(4)

```
2801 TCGGTGTGGCGACGCGCTGCCGCGCGGACACGCAGCCCGACTTCCCGCTGCTCGACTTCGATACCGCGGCCGA  2900
     euAlaTrpArgAspAlaLeuProArgArgIleArgAlaThrArgAlaGluLeuGluThrGlnProAspPheProLeuLeuAspPheAspThrAlaAlaGl  196
193

2901 ACTGCTGTACCGCTTCATCACCGACCTGCAGGAATACGGGGACGAGCCGCACGAGCCGAACGCTGGATCGAACGCTAC  3000
     uLeuLeuTyrArgPheIleThrAspLeuGlnGluTyrAlaAlaThrTyrAlaAlaThrHisGluArgGluArgTrpIleGluArgTyr  229
196

3001 GAGCCGCACCAACAAAGGCCTGCCACGATCCGCCACGGTGATTCTCGCGCTGGTTCTGAATGAGACTGGTGGCCGA  3100
     GluProHisGlnLysThrAlaAlaThrValIleLeuAlaLeuGlyTrpPheTrpIleGluThrAlaTrpProS  263
230

3101 GCGGGCGTGATGTGTGCTGAACGCGGACTTGCGCCCGACCGGATGGGGATGGGCACGGC  3200
     erGlyValMetLeuValIleLeuAsnAlaAlaAlaThrCysAlaLeuAlaSerSerAlaProArgProThrAlaMetAlaAlaGlnMetGlyThrAl  296
263

3201 GCTGGCCGTCTGACCGGCTTCCTGCTGACGTTCGGCATCTACCCGGATCGACGGCTTCGTGTGCCGTTGCTCCGGATC  3300
     aLeuAlaValCysThrGlyPheLeuThrPheGlyIleTyrProArgIleAspGlyPheValLeuLeuCysAlaAlaLeuAlaProLeuLeuAlaIle  329
296

3301 GGCATCTACATGTCGCTGAAGCCGAAGCTCGCGCTATCGTTCTTCTGCTTCCTGCCGGCCCCGACAGCATCACGCACTACGA  3400
     GlyIleTyrMetSerLeuLysProLysLeuAlaGlyTyrGlyGlyAlaIle***  346
330
     fadD 3401 TCCCACGAGCTTCATGAACGACTTCGTTGTCGATGCTCGTCTCGGGATCGCGGTTCGGCGTTCGCCGACCGGCCGTGGCTC  3500
              MetAsnAspAlaLeuAlaLeuLeuSerMetLeuValSerAlaIleAlaPheAlaValLeuPheProProThrAlaProTrpLeu  29
1

3501 AAGAAACGCCTGTTCGCGACCTGCTCACCAGGCCGTCGCCGGACTGGCCACGGCTTCGAGAGCGGCGGCGACC  3600
     LysLysArgLeuPheAlaAspLeuArgHisGlnAlaValAlaAlaCysHisAlaAlaGlyLeuArgThrArgPheGluSerGlyAlaArgAspL  63
30

3601 TGATGTACCAGGCGCACGCTGTCGCGACCCGAGTGCAGGCGACCCGTGCTGGATGTTCGGGTGCTGAAACCGGAATGGCCATCGA  3700
     euMetTyrGlnAlaHisThrLeuSerAlaAspHisProThrCysSerAlaThrProCysTrpMetPheAlaValLeuGluThrGlyAsnAlaAlaIleAs  96
62
```

FIG. 4(5)

```
3701 CCTGCGCCACGAGCTGGCAACGCTGCCGTCCGACCCGGCTACGGCCGTCGCCGTGGCGCCGCGGACGACGCCGTTGCGATCGAAACGATGCGGCCGCCGTGTCGTCG  3800
  96 pLeuArgHisGluLeuAlaThrLeuProSerAspProAgrTyrAlaProThrThrProTrpArgArgAlaIleGluThrMetArgAlaAlaLeuSerSer         129

3801 CTGTTCGCGGACGCCGAACGTTTCGATGCAACGCCGGCCGGTAAACGCTCGACGGCAGACGCTGATCGAACGGAGACCCGGTCGAGACGCAGACGCATTACGCCGA  3900
 130 LeuPheAlaArgProAspAlaGluArgPheAspAlaThrLeuAlaAlaValAlaAsnAlaIleAspAlaThrLeuArgGlnThrLeuAspAlaPheThrProT    163

3901 CGGGCGAGGAACGCGACCGGCTGAGCGTGAGCCATCTGCATTTCGTGCCCACGACACTGTGCGCCACGCTGCTCGATCCGGAACCGCTCGCCGCGCTCAACCG     4000
 163 hrArgGluGluArgHisArgLeuGlnArgIleLeuSerHisLeuHisPheValArgThrAlaLeuLeuAspProGluSerProLeuAlaAlaLeuAsnAr      196

4001 CAACCGCCCCGTCGTCCCCAACCAGGAGCCTCGTCATGATGCCGTGAAATCGCCTACATGCCCACGGTGGTGCTGATGTTCGTCC                        4100
 196 gAsnArgProValArgProGlnProGlyAlaSerSer***                                                                  208

4101 TCGGGCGCTCGGACTGGGCGTCGACCCGTCGCTCGCCTATACGGGCCTCGTCGTTCCGGGCCTGCTTCGACCGGTCATTCT                            4200

4201 CTGCATTTGCGGCGACTGAGTCTTGCGCGTTACGCGTTGATTCCGAACCATCATGAGTTCTCAGAAAACTCTTCGGCTTCGTCGGACCGCGTCATTCT           4300

4301 TCTCGTCGGGATCCTGATCGGGCGCTCGCTCGTGTGGGTGCACTACATGGACGATCCGTGGACGCGCACGGGACGCGTCAAGGCGTCAACGTCGCG             4400
                                                                                                    fadE 4401 CCGGACGTGTCGGGCGGGATCGTCGAACTGCCGTGCATGACGAACCAGCTCGTGAAAAGGGCGACCTGATCATGCAGATCGATCCGTCACATACCAGA          4500
   1                                                                       MetGlnIleAspProSerHisTyrRgLNI        10

4501 TCGCGGTCGAGCAGGCCGCGGACGCGGCCGCGAGCTGCAGATGCCGAGCTGCCGCGATCTCGATGCCTCGTGTGTCGAA                             4600
  10 IleAlaValGluGlnAlaGlnAlaValAlaValAlaAlaAlaArgSerCysArgArgArgGlyArgArgGlyArgArgAlaAspLeuAspAlaLeuValSerLy    43

4601 GGAAAACGCGAGAACGCCGCACAGTGCTGCGAGCGCCGATGCACAGGCGATCCCGCGCTCGATGCGCGAAGCTCAACGCTCGAGCGC                     4700
  43 sGluAsnArgGluAsnAlaAlaHisSerAlaSerSerAlaAspAlaGlnTyrGlnGlnAlaIleAlaAlaLeuAspAlaArgSerThrLeuGluArg           76
```

FIG. 4(6)

```
4701 AGCCGGTCGTCGCCGGTCGACGGCTACATCACGAACCTGCGAGACGTTCAAGGGCAACTATGCGGTGGCCGGCCAGGCGAAGCTCGCGATCGTCGACA  4800
 77  SerArgValValAlaProValAspGlyTyrIleThrAsnLeuGluThrPheLysGlyAsnTyrAlaValAlaGlyGlnAlaLysLeuAlaIleValAspS   110

4801 GCCACTCGTTCTGGGTCTACGGCTACTTCGAGGAAACCAAGTGCCGCGTGAAGATCGCCGGCCGTGAAATGGGCTGATGAGCGGGCGGTGAT  4900
110  erHisSerPheTrpValTyrGlyTyrPheGluGluThrLysLeuProArgValLysIleGlyAlaProAlaGluMetArgLeuMetSerGlyGlyValMe  143

4901 GAAGGGCCATGTCGAAAGCATCTCGGCGCATCTACGATCGGAGACAACCCGACCTGAACCCGACCTCCGAGACGTGAACCTGAACCCGACCTTCAACTGGGTGC  5000
143  tLysGlyHisValGluSerIleSerArgGlyIleTyrAspArgAspAsnProGlnSerArgAspLeuValArgThr***                           168

5001 GCCTCGCGCAGGCGTGCCGGTGCGATCAGGATCGACGAATGGCCGGCGACGTGGTCGTGTCGGCGGGTACGACCTGCACGGTCATCATCGARCCGGA  5100

5101 CAAGCAGAAGAAGTCGTAAGCGCAACGCGCGGCATCCCGCCGCGTCACTCCCAGAAGAACCGGTAAGGCAGGAACGGCGACGGGCCGA  5200

5201 GCCCCGCTTCGCGGATCATGTTGCGCAACCGGATCGCAAAGCGATGGCGCGATCACATACGGGCCGCCGCACGTACGGCAC  5300

5301 GCGTTGCAGGGCACGAACTGGAGCAGCCCATCGCGAACAGCACGAGCCACTGGAAGCGCAGCCCCGCATAGCTGACCCGCGAGCGCGAAACTCGCGGATC  5400

5401 TCGGCAGGCGAACAGGAACACGAGCGTGCCGCGGCATGC                                                              5437
```

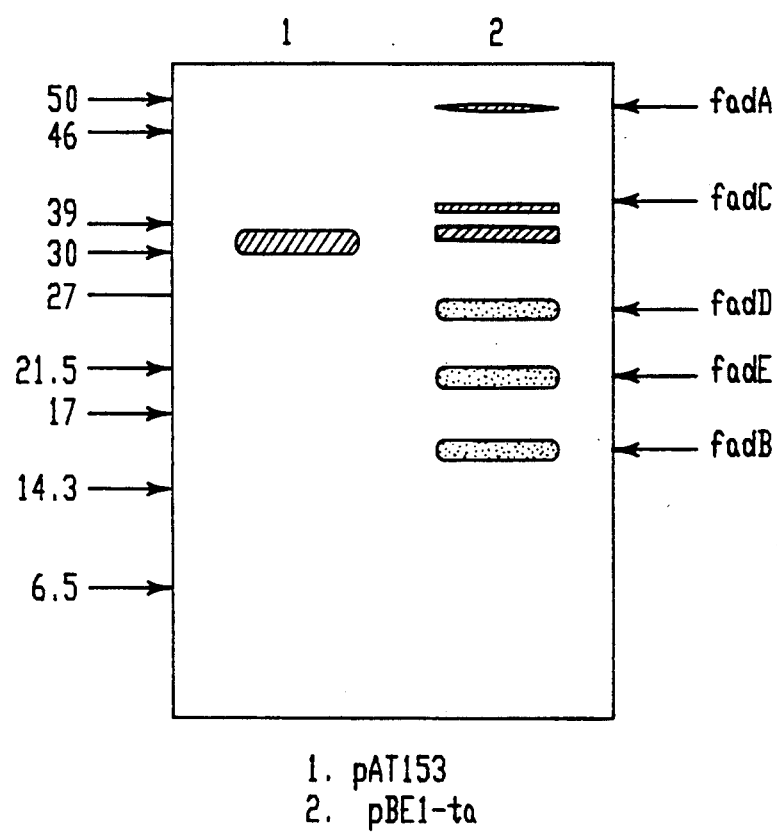

FIG. 7(1)

```
    GGA TCC ACA CCG CGC AGT CTG GCG GCA CTA TCC AGA TAT CGT TTT CCG

CAC GAC AAA TCA CCG CCC CAT AGA GGG CAA CGA TCA GTT GTC CCT TGC GGT GGG

TAT GAA CCG GCA CTT CTG CCG CGT AAA CAA CGA AAT CAA TAT GCC GCG CGA CGG

CAG GGC TCG GCG TGC TAT CGG GAT CAA ACA GGG TAT GGG CAA GTC TGG ATG GCA

TCT CAT TGG CAA CAT TTA GGT ATT TTT TGA CAG AAT AGA GTA TTT AAG GAG ACG

CGC AAA GCG GAA TAA TTC CCG GCA TGA GCA CAT TAA CTT CCC ATC ACA GCC GTT

TTT TAC ACG GCA TAA GCC GTT GGT CAG GGC CGC ATA GCC TCT CCC TGC GCT GCT

Met Pro Cys Ser Ile Pro Ser Gly Val Leu Pro Pro Arg Cys
TGA GCG ACG CCC ATG CCC TGC TCT ATT CCG TCA GGA GTT TTG CCG CCG CGA TGC

Tyr Arg Leu Ala Gly Thr Val Ala Gly Ala Gly Ala Thr Val Leu Ile Val Pro
TAT GCG CTG GCC GGT ACC GTG GCC GGC GCG GGG GCC ACG GTA TTG ATT GTG CCG

Thr Phe Val Asn Thr Pro Ile Leu Cys Ser Val Ile Leu Ala Gly Trp Ile Thr
ACG TTT GTG AAT ACG CCA ATT CTA TGT AGC GTG ATT CTG GCT GGC TGG ATC ACC

Phe Cys Leu Tyr Leu Ser Leu Leu Gln Arg Thr Pro Arg Ala Tyr Ala Phe Val
TTC TGC CTC TAT TTA TCC CTG CTT GAA CGC ACG CCC CGC GCC TAT GCC TTT GTG

Leu Ala Gly Tyr Thr Ala Ser Leu Ile Gly Phe Pro Ala Val Ala Asp Pro Gly
CTG GCC GGT TAT ACC GCA AGC CTG ATT GGT TTT CCC GCC GTC GCC GAT CCC GGC

Thr Cys Leu Thr Ser Pro Ser Ser Gly Tyr Arg Lys Ser Arg Ser Val Ser Ser
ACG TGT TTA ACA TCG CCC TCA TCC GGG TAC AGG AAA TCG CGA TCG GTA TCG TCT

Ala Pro Arg TER
GCG CCG CGC TGA TTC ACC GCT ACA TTT TAC CTG CCC GGA TAT CAG GGC TGT TCA

ACA GCA ATT TAG CCC AGA CGC TGC ACG CCG CGC GCC AGG ATT GCC GAC ACC CTG

GCA GGC AAG GCC GAC GCG CAG TCT GAG CCG CTG CAT CTG GCG CTG GCG CTA CAG

TTT CTT CAG GGC ATC AGC CAC CAT ATC CCG TAT GAT TTT GCC CTT TCG GTT CCG

GCC CGC CAG GCC AGG AAA GCG CTC CAT GAC AGG CTG GCG CGG TTA GTG ATT GTC
```

FIG. 7(2)

```
AAC GGC GAA GTG CGC GAT CGT TTG CAG ATC ATC GCC GGG ATG CCC GCC GCG ATG

CAG ACT CTA CTG AAT GAC GTG CAG GCC TGG CTG ACC TGC GAC GAT ACC GGC CAA

CGC AAA AAC GCC GCA GAA GCG CTG CAA CAG CGC AGC GCA GTT AGC GCG GCG GCT

CGC GGC GCA GGC GCT GAC CTT TGA AGA TGC GCT GCG GGT AAA TTT CTT ACG CTA

CAT CGC TGA GTT GAT TAC CCT CCT GCA GCA GTG TGA GCG GCT TTC GGA GGC C
```

```
                                                             Val Arg Arg Gln Asp
ATT CAT CAC GCC AGA CCT GCG CCA GCG CAT GGA AGA ATC GTG CGG CGA CAG GAT

Thr Phe Ser Ile Ala Ile Pro Ser Ser Ala Ala Arg Thr Ala Leu Gly Ala Phe
ACG TTT TCC ATC GCG ATC CCC TCC AGC GCC GCC CGC ACG GCG CTG GGC GCT TTT

Val Ile Ile Leu Ser Gly Cys Leu Leu Trp Ile Tyr Ser Ala Trp Pro Asp Gly
GTC ATC ATT CTG AGC GGC TGT CGT CTA TGG ATT TAC TCT GCC TGG CCC GAT GGC

Gly Thr Ala Val Ser Ile Leu Gly Val Cys Cys Thr Leu Phe Gly Ser Phe Asp
GGC ACG GCG GTG TCG ATT CTC GGG GTT TGC TGC ACG CTG TTT GGC AGT TTC GAC

Thr Pro Ala Pro His Ile Val Lys Tyr Ile Ile Gly Ser Val Trp Gly Val Val
ACG CCG GCC CCG CAT ATT GTG AAA TAT ATT ATC GGC TCT GTC TGG GGC GTA GTG

Ile Ser Leu Ile Tyr Ser Phe Ala Leu Leu Pro Pro Leu Ser Asp Phe Pro Val
ATA AGC CTT ATC TAT AGC TTC GCC CTG CTT CCT CCG CTC AGC GAT TTC CCC GTG

Leu Val Ala Val Leu Ala Pro Val Tyr Leu Leu Ala Gly Ser Leu Gln Ala Arg
CTG GTG GCG GTG CTT GCC CCG GTC TAT CTG CTT GCC GGA TCG CTG CAG GCG CGG

Pro Pro Thr Thr Phe Met Ala Met Gly Ile Thr Leu Thr Leu Pro Val Leu Cys
CCC CCC ACG ACC TTT ATG GCC ATG GCC ATG GGG ATC ACC CTG CCG GTA CTG TGC

Glu Leu Gly Ala Arg Tyr Ser Gly Asp Phe Ala Asp Ala Ala Asn Thr Ala Ile
GAG CTG GGC GCG CGC TAC AGC GGC GAC TTC GCC GAC GCG GCC AAC ACC GCG ATC

Ala Leu Phe Phe Ala Thr Gly Phe Ala Val Ile Gly Met Ser Leu Leu Gln Thr
GCC CTG TTT TTC GCG ACC GGC TTT GCG GTT ATC GGC ATG AGT CTG CTG CAA ACC

Val Gln Ala Asp Ala Ala Ile Lys Arg Leu Leu Lys Leu Cys Gln Arg Asp Ile
GTA CAG GCG GAC GCG GCG ATA AAG CGT CTG CTG AAA CTG TGC CAA CGC GAT ATT
```

FIG. 7(3)

```
Arg Arg Ser Val Ser Gly Ala Phe Lys Gly Asp Glu Thr His Trp Thr Asn Leu
CGC CGC AGC GTG AGC GGC GTA TTT AAA GGC GAT GAA ACG CAC TGG ACC AAT CTG

Met Ile Asp Arg Gly Ala Leu Leu Leu Pro Arg Leu Arg Ala Ala Gly Ser Pro
ATG ATC GAC CGG GGC GCT CTG CTG CTG CCA CGC TTG CGC GCA GCG GGC AGT CCT

Pro Pro Gly Arg Ser Ile Ala Trp Cys Thr Phe Cys Ala TER
CCG CCC GGG CGC TCG ATC GCC TGG TGC ACT TTC TGC GCA TAG GCC TCT GCG TTA

TGC GCC TGC GCC GTT GCG AAA CGC CCG CCG GCA GCG ATA TCC ACG AGG TGC TTT

CTC GTC TTA CCC ACA CAA CGG AGA CCG AAG CCT TAC GCG AGC GCA TTG CCG CCA

TGG CGA ACC GCT GCT TGC CCG CGA GGG AGG AAC AAT CAT GCC AGT TTG TCG ACC

GAC TGG TCG ATC TGC ACT GCG CGT TAC GGA CGC AGA ACG AGG AAC CCA CCC ATG

ATA AAT GAC ATC AAT ATC GGG GGC GTT TTT ATC CCC GGA CTG CTG CTG ACC GCG

CTC ATT GCC CTG GTC TGT ACG CTG TTA CTC GTA CCG CTT TTC TCT GCA GCA GGC

TTT ACC GCC GCT TGC CCT TAC GCC CGC TGC TTG ATG TTT CAA CCT ATA TCG TGA

CCT TTT TCC TGC TTT TGC AGG GCC TGA CCA CAC TGG GGT TAT TCG CAT GAA ATC

TTT TTT CTC TTT GCT GGG CCG TTA CGC GCT GAC GTT AAT CGC AGT AGC GGT AGC

Val Ala Phe Ile Phe Trp Lys Gln Tyr Ala Gln Thr Pro Trp Thr Arg
GCC TGC GTG GCG TTT ATT TTC TGG AAA CAG TAT GCG CAG ACG CCC TGG ACG CGC

Asp Gly Arg Val Arg Ala Asp Val Val Gln Ile Ala Pro Asp Val Ser Gly Pro
GAT GGC CGG GTT CGG GCA GAT GTG GTG CAG ATT GCG CCG GAT GTT TCC GGG CCG

Val Ser Ser Val Ala Val Arg Asp Asn Gln Trp Val Asn Arg Gly Asp Val Leu
GTG AGC AGC GTG GCG GTG CGG GAT AAT CAG TGG GTT AAC CGC GGC GAT GTG CTT

Tyr Ala Ile Asp Pro Arg Trp Leu Lys Leu Ala Val Leu Ser Ala Gln Ala Asp
TAT GCC ATC GAC CCG CGC TGG CTG AAG CTG GCG GTG CTC AGC GCG CAG GCC GAC

Val Glu Ala Lys Arg His Glu Met Leu Met Arg Gln Asp Ala Ala Pro Pro Arg
GTC GAA GCA AAA CGT CAT GAA ATG CTG ATG CGC CAG GAT GCC GCC CCG CCA CGC
```

FIG. 7(4)

```
Ala Leu Ile Lys Gly Val Ile Ser Gly Glu Asp Ile Gln Gln Thr Gly Ser Ala
GCG CTC ATC AAA GGG GTC ATT TCC GGC GAG GAT ATC CAG CAA ACA GGC AGC GCA

Ala Ala Val Arg Gly Gly Gln Leu Ser Gly Gly Ala Gly Cys Ala Gly Thr Gly
GCT GCT GTT CGC GGC GGC CAA TTA TCA GGG GGC GCT GGC TGC GCT GGA ACT GGC

Ala Val Lys Leu Ile Pro Cys Asn Ala Thr Pro Pro Leu Pro Ala Thr TER
GCA GTG AAA CTT ATC CCA TGC AAC GCT ACG CCC CCG TTA CCG GCT ACG TGA CGC

ATC TTC GGC TCC GCC CGG CGA CTA CGC CGC GGC GGG AGA AAC AAA GGT CGC CGT

GGT CGA TGC GCA CAG TTT CTG GGT GGT GGG CTA TTT TGA GAG GAC AAG CTG CGT

CAT ATT CGC GTC GGG AGC GCC GCA CAC ATT TCT CTG ATG GGG TTT GAC CCG CTC

ATC ACC GGG CAC GTG GAG AGT ATC GGC CGG GGG ATC GAT GAT AGC AAT GAC GAG

ACC GGC GGG CTG GGG CTG CCG GAT GTC AAT CCC ACC TTC AGC TGG GTG CGA CTT

GCG CAG CGA GTC CCC GTT CGT ATA CAG TTA GAT AAG ATA CCG GAA GGG ATT GAA

CTG GTG GCG GGA CTA TCC GCC AGC GTT TCC ATC CTG CCT GAA AGC CTA GAC GGC

GGG CGT AGC GGA GGA TCG GGC TAC GTG GCT CAG GCT ATC CAC CCA TAG TGG ACC

CGA GAC TCA ATG AGG AAA CGA CGC TTC TGC AAA AAT ATC TGG CCC GAA TAT ACC

GAA CTC GAT ATT CTG TAA TGC TTT GTA TTT TTT GTG AAC AGG AAA AAG TAT GCT

TAG TAC GTT ACC CGA TTT ACA CAG AAG TTT TGC AGA GCA ACT CAA GTA TT
```

FUSARIC ACID RESISTANT GENES

BACKGROUND OF THE INVENTION

1. Field of the Invention

The present invention relates to fusaric acid resistant genes cloned from fusaric acid decomposing or detoxifying microorganisms, plasmids having the genes, host cells transformed by the plasmids, proteins having amino acid sequences specified by the base sequences of the genes, respectively and capable of participating in the decomposition or detoxification of fusaric acid and production processes of the proteins, and utilization of the genes and proteins.

2. Description of the Related Art

Wilting disease which causes plants to wilt or droop to die is a serious disease for cucurbitaceous plants such as cucumber, water melon and melon and solanaceous plants such as tomato and egg plant. Wilting disease is induced by soil-inhabiting fungi of the genus Fusarium. Soil sterilization and the avoidance of continuous cultivation of a particular crop are the only measures effective for the control of wilting disease caused by fungi of the genus Fusarium. These measures are however difficult to practice for most farmers from both technical and economical viewpoints, yet any effective control method which may substitute for these measures has remained unavailable.

Fusaric acid (5-n-butylpicolinic acid) is known to be a toxin which is produced by plant pathogenic fungi of the genus Fuarium and non-specifically acts on a wide variety of plant cells [Wood, R.K et al., "Phytotoxins in plant diseases", Academic Press, New York (1972); Durbin, R.D., "Toxins in plant diseases", Academic Press, New York (1982); Gaumann, E., Phytopathology, 47, 34 (1958)]. Although the mechanism of action of fusaric acid has not been fully elucidated, fusaric acid is known to exhibit, for example, strong toxicity on tomato callus cells and tomato stems and leaves, to increase the plasma membrane permeability of tomato cells whereby the exudation of the tissue fluid is induced to accelerate death [Matsuo, Hayami et al., "Sakumotsu no Fusarium Byo (Fusarium disease of crops)", Zenkoku Noson Kyokai (National Association of Agricultural Communities)], to inhibit germination and rooting of barley [Foy, C.L. and Change, I., Adv. Pestic. Sci., 3, 499 (1979)], and to show proliferation inhibitory effects against fungi and bacteria [Kalyamasundram, R., Plant Dis. Probl., 1, 142 (1970)].

On the other hand, there are some varieties of tomato which exhibit resistance to diseases caused by fungi of the genus Fusarium. Fusaric acid is metabolized and converted to N-methylfusaric acid amide in plant tissues of these resistant tomato varieties. A variety with stronger fusaric acid resistance shows greater fusaric acid converting action. As a matter of fact, plants having such resistance to fusaric acid have been found to be resistant to wilting disease caused by *Fusarium oxysporium* [Shahin, E.A. and Spirey, R., Theor. Appl. Genet., 73, 164 (1986); Toyoda, H., et al., Phytopathology, 78, 1307 (1988)].

Fusaric acid is known to exhibit not only wilting toxicity against plants but also toxicity against microorganisms such as bacteria. As fusaric acid resistant microorganisms capable of growing on or in a culture medium containing fusaric acid, the present inventors isolated several types of microorganisms from soil. The isolation methods, mycological characteristics, fusaric acid resisting mechanism, etc. of these fusaric acid resistant microorganisms are disclosed in detail in Japanese Patent Application Laid-Open Nos. 198974/1988 and 198987/1988. One of the above fusaric acid resistant microorganisms has been identified as *Pseudomonas cepasia*. This bacterium has been found to have fusaric acid decomposing ability and also to be able to grow using fusaric acid as a sole carbon source, in other words, to have fusaric acid assimilating ability.

It may hence be considered feasible to avoid development of an infectious disease by a fungus of the genus Fusarium-such as wilting disease which is very difficult to control-provided that fusaric acid which is the non-specific toxin produced by the fungus of the genus Fusarium can be decomposed and eliminated. For this purpose, decomposition or detoxification of fusaric acid by one of the above fusaric acid resistant microorganisms can be an effective means. It is however very difficult to bring such a fusaric acid resistant microorganism into contact with fusaric acid produced within a plant due to infection by a fungus of the genus Fuarium.

As a means for overcoming such a difficulty, it has been a practice to some extent to breed a plant, which can decompose or detoxify fusaric acid, by isolating a fusaric acid resistant gene from one of the above fusaric acid resistant microorganisms and then introducing the gene in a plant. Plants having such fusaric acid resistance can be used as effective means for the control of wilting disease caused by a fungus of the genus Fusarium. Knowledge on the fusaric acid resistant gene and its structure is indispensable to make use of such a genetic engineering technique.

SUMMARY OF THE INVENTION

An object of the present invention is to provide a gene capable of participating in the decomposition or detoxification of fusaric acid derived from microorganisms and effective for the control of plant diseases such as wilting disease by fungi of the genus Fusarium and also information on the structure of the gene.

Another object of the present invention is to provide a protein which is coded by the gene and can participate in decomposing or detoxifying fusaric acid.

The present inventors have proceeded with an extensive investigation to achieve these objects. As a result, it has been found that a fusaric acid resistant gene exists in a fusaric acid resistant microorganism, namely, a microorganism capable of growing on or in a culture medium containing fusaric acid and of decomposing fusaric acid or detoxifying it to plants and can be obtained from such a microorganism.

It has also been found that a protein capable of participating in the decomposition or detoxification of fusaric acid can be obtained from the above fusaric acid resistant gene.

In one aspect of the present invention, there is thus provided a fusaric acid resistant gene derived from a fusaric acid decomposing or detoxifying microorganism.

In another aspect of the present invention, there is also provided a DNA fragment comprising a fusaric acid resistant gene derived from a fusaric acid decomposing or detoxifying microorganism.

In a further aspect of the present invention, there is also provided a plasmid comprising a fusaric acid resistant gene derived from a fusaric acid decomposing or detoxifying microorganism.

In a still further aspect of the present invention, there is also provided a host cell comprising a plasmid which has a fusaric acid resistant gene derived from a fusaric acid decomposing or detoxifying microorganism.

In each of the above aspects of the present invention, the fusaric acid decomposing or detoxifying microorganism may preferably be Pseudomonas cepasia or Klebsiella oxytoca.

In a still further aspect of the present invention, there are also provided the base sequences of a DNA fragment derived from Pseudomonas cepasia and capable of coding a protein, which can participate in the decomposition or detoxification of fusaric acid, and the amino acid sequences of a protein capable of participating in the decomposition or detoxification of fusaric acid, said amino acid sequences being identified from the above base sequences.

In a still further aspect of the present invention, there are also provided a DNA fragment derived from Klebsiella oxytoca and capable of coding a protein, which can participate in the decomposition or detoxification of fusaric acid, and the restriction map of the DNA fragment.

According to the present invention, the whole base sequence of the DNA fragment of 5.4 kb [SEQ ID NO: 1] containing the fusaric acid resistant genes derived from Pseudomonas cepasia has been determined, resulting in the identification of the structure of the fusaric acid resistant qenes and also the structure of those proteins (i.e., amino acid sequence) [SEQ ID NOS: 2-6]. In addition, the entire base sequence of the DNA fragment of 3.6 kb [SEQ ID NO: 7] containing the fusaric acid resistant gene derived from Klebsiella oxytoca has also been determined. The gene structure and, moreover, the protein structure (amino acid sequence) [SEQ ID NOS: 8-10] have also been specified.

It is possible to obtain fusaric acid resistant plants by introducing these fusaric acid resistant genes in plant cells. Since fusaric acid resistant plants obtained in this manner are resistant to wilting disease and the like caused by fungi of the genus Fusarium, the problems in controlling diseases caused by such fungus of the genus Fusarium have been overcome.

It is also feasible to mass-produce proteins, which are coded by the above fusaric acid resistant genes and can participate in the decomposition or detoxification of fusaric acid, by a genetic engineering technique and to use them for the control of disease caused by fungi of the genus Fusarium.

BRIEF DESCRIPTION OF THE DRAWINGS

The above and other objects, features and advantages of the present invention will become apparent from the following description and the appended claims, taken in conjunction with the accompanying drawings in which:

FIGS. 4-1 to 4-5 depict the base sequence [SEQ ID NO: 1] and amino acid sequences [SEQ ID NOS: 2-6] of a DNA fragment containing a fusaric acid resistant gene derived from Pseudomonas cepasia. The base sequence contains 5437 bases, extending from the EcoRI site to the SphI site. Under the base sequence, the amino acid sequence of the estimated proteins are shown. Genes (fadA, fadB, fadC, fadD, fadE) are shown above individual initiator codons. The underline drawn immediately before each initiator codon indicates an estimated ribosome-binding position (SD sequence). The upper numbers show base pair numbers, while the lower numbers indicate the corresponding amino acid numbers;

FIG. 5 shows the results of an analysis of proteins which have bearing on fusaric acid resistance. In the drawings, the thick lines indicate DNA fragments inserted in the mutant plasmids shown on the left side. The 5.4 kb EcoRI/SphI fragment which is a part of the inserted DNA fragment (8.4 kb) is shown. The alphabet letters above the thick lines indicate cleavage sites for the following endonucleases: Ap: ApaI, Bp: BstPI, E: EcoRI, P: PstI, Sm: SmaI, Sp: SphI. The parentheses indicate that reading frames were shifted by cleaving the fragments with the corresponding endonucleases and then applying Klenow enzyme treatment. Further, for example, E(Sm) designates that reading frames were shifted by cleaving the fragment with SmaI and then inserting an EcoRI linker there. The fusaric acid resistance of recombinant strains of Escherichia coli, said recombinant strains having been obtained by transforming Escherichia coli with those mutant plasmids, is shown on the right side, respectively. The arrows in an upper part of the drawing indicate the open reading frames (ORFs) in the DNA fragments. Of these ORFs, the ORFs (fadA, fadB, fadC, fadD, fadE) which were actually found to have bearing on fusaric acid resistance from an analysis of fusaric acid resistance of recombinant strains of Escherichia coli—said recombinant strains having contained deleted plasmids, respectively—are shown by the thick arrows;

FIG. 6 schematically illustrates the results of an analysis of in vitro transcription and translation products. The arrows on the left side designate the migrated positions of molecular weight markers which were concurrently subjected to electrophoresis. The values are the molecular weights of the molecular weight markers. The arrows on the right side indicate the migrated positions of five proteins which have bearing on fusaric acid resistance; and FIGS. 7-1 to 7-3 show the base sequence [SEQ ID NO. 7] and amino acid sequences of [SEQ ID NOS: 8-10] a DNA fragment containing a fusaric acid resistant gene derived from *Klebsiella oxytoca*.

DETAILED DESCRIPTION OF THE INVENTION AND PREFERRED EMBODIMENTS

Figure 1:
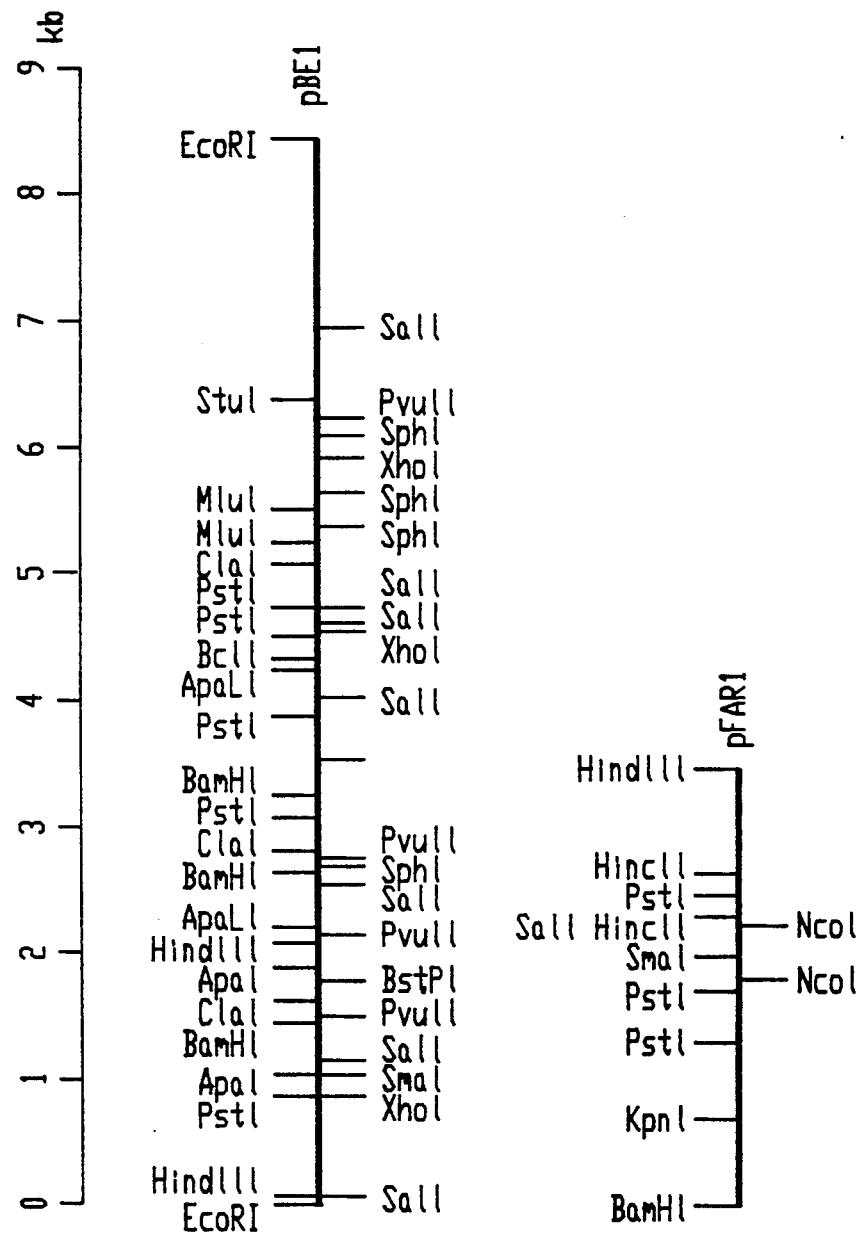
FIG. 1 shows the restriction maps of DNA fragments which contain different fusaric acid resistant genes, respectively. In the drawing, the thick lines indicate the DNA fragments to be inserted, pBE1 a plasmid containing the fusaric acid resistant genes derived from Pseudomonas cepasia, and pFAR1 a plasmid containing the fusaric acid resistant genes derived from Klebsiella oxytoca.

Several types of bacteria and fungi have already been found as fusaric acid resistant microorganisms by the present inventors, including, for example, bacteria belonging to the genus Pseudomonas and those belonging to the genus Klebsiella. Among fusaric acid resistant microorganisms usable in the practice of the present invention, preferred bacteria belonging to the genus Pseudomonas include *Pseudomonas cepasia*, especially *Pseudomonas cepasia* UK-1 strain (FERM BP-1385). On the other hand, preferred bacteria belonging to the genus Klebsiella include *Klebsiella oxytoca*, particularly *Klebsiella oxytoca* HY-1 strain (FERM BP-3221). The mycological characteristics of the above bacteria, their culture conditions, and the decomposition or detoxification of fusaric acid by them are disclosed in detail in Japanese Patent Application Laid-Open No. 198974/1988 and Japanese Patent Application No. 22957/1990.

*Pseudomonas cepasia* UK-1 strain can decompose and detoxify fusaric acid and can grow using fusaric acid as a sole carbon source. On the other hand, *Klebsiella oxytoca* HY-1 strain can decompose and detoxify fusaric acid but cannot grow using fusaric acid as a sole carbon source.

The fusaric acid resistant gene of the present invention can be obtained by preparing a gene library of one of the above microorganisms, which has fusaric acid decomposing or detoxifying ability, using *Escherichia coli* as a host and then screening a fusaric acid resistant recombinant strain of *Escherichia coli* from the gene library. In general, the gene library can be prepared by cleaving a DNA, which has been isolated from a cell of the microorganism, with a suitable restriction enzyme, i.e., restriction endonuclease (hereinafter simply called "endonuclease" for the sake of brevity), inserting a desired segment in a vector and then transforming *Escherichia coli* with the resultant recombinant plasmid. Since host *Escherichia coli* cannot grow in a culture medium containing fusaric acid, only the recombinant strain of *Escherichia coli*, said strain containing the gene capable of participating in the decomposition or detoxification of fusaric acid, can grow in the culture medium.

By collecting the plasmid from the fusaric acid resistant recombinant strain of *Escherichia coli* which has been obtained as described above, the restriction map of the inserted DNA fragment is prepared. After DNA fragments which have been obtained by cleaving the inserted DNA fragment by various endonucleases on the basis of the restriction map are inserted in vectors, *Escherichia coli* is transformed, followed by the screening of clones which exhibit resistance to fusaric acid. With respect to the clone having the shortest inserted DNA fragment out of the clones capable of exhibiting fusaric acid resistance, the base sequence of the shortest inserted DNA fragment is determined.

An analysis of the base sequence so determined makes it possible to estimate protein-coding regions (ORFs: open reading frames), so that the amino acid sequence of a protein coded by the respective ORFs can be elucidated. In addition, mutant genes with the reading frames of the individual ORFs shifted are prepared by conducting cleaving at cleavage sites, which are present in the respective ORFs, with an endonuclease, converting the cleaved ends of the resulting fragments to blunt ends with Klenow enzyme and then re-ligating the fragments together into a circular form. Strains of *Escherichia coli*, which have been transformed by these mutant genes, respectively, show no fusaric acid resistance. This indicates that the individual ORFs are coding a protein capable of participating in the decomposition or detoxification of fusaric acid.

The followings are an exemplary base sequence relating to fusaric acid resistance, which had been determined in the above-described manner by using *Pseudomonas cepacia* as a source microorganism, and an illustrative amino acid sequence derived therefrom:

(Base sequence)

Formula (VI) [SEQ ID NO: 11]:

ATGGCGCGCGTGGCCCGCTCGGCCGAATTGCCACAGATCA

ACGGCAACCTCTCGCTGATGCGCCAGCACTGGCCGGACAA

CGTCTATTACGGCCCCGGCCCGCTCGCGAACACCGACACC

TGGAACAACACCGGCACGCTCGGCCTGTCCTACCACCTCG

ACCTGTGGGGCAAGGACAAGAACGCGACCGAGCGCGCGCT

CGATACCGCGCACGCGACCGCCGCCGACGCACGCGCGGCG

AAGCTCGAACTCGAAGTCAACGTCGTGCGCGCGTACGTCG

GCATGTCGATGAACTACGCGCTGCTCGACCTCGCGCACGA

AACGTTCGAACGCCAGCGCTCGCTCGCCGATCTCGCGCGC

AAGCGGCTGCAGGCTGGCCTCGGCACGCAGCTCGAGGTGA

-continued

GCCAGGCGGAATCGACGCTGCCCGACTATGAGCGCCAGAT

CGACAGCTACGAGGAAGCGATCCAGCTCGCGCGGCACCAG

CTCGCCGCACTGGCCGGCAAGGGCCCGGGCGCCGGCGATG

CGATCAAGCGGCCTCGGCTGTCGCTCGACGCACCGGCCGG

CTTGCCGTCGGCGATGCCGGCCGACCTGCTCGGCCGCCGC

CCCGACGTCGTCGCGGCACGCTGGACGGTCGACGCGCAGG

CGCGCGGCATCGACGTCGCAAAGGCTTCGTTCTATCCGAA

CATCGACCTGCTCGCGACGGTCGGCGGCTTCGGCGTGACC

GCGCCGTTCACCGACTTCCTGCGCGCGATGAACGGCGGCT

GGACGGCCGGCCCCGCGCTGTCGCTGCCGATCTTCGAAGG

CGGCCGGCTGCGCGCGCAGCTCGGCGCGGCGAATGCCGGC

GTACGACCAGGCGGTCGAGCAATACAACCAGACGATCGTC

GGCGCGCTCAAGGACATCGCCGACCAGGTCGTGCGGATCC

GTTCGCTCGATACGCAGAAGAAGGACGCCGCACGCTCGGT

GGCCGCCAACGACCGCAGTTACCAGCTGTCGCGCGAAGGC

TTCCGCCGCGGCCTGACCGACTACGTCAACGTGCTGGTCG

CGCAGCAGCAATTGTTGGCGCGCACAGGAAACGGCCGCCG

CATCGATCGGAACGCCTCGCCGCGCACGCTCAACTGATGG

CCGCGCTGGGTGGCGGCGTCGAGACGGGCACGGACGTGCC

GGGCAGCCAATCGTCGCATGGCGAATCCGCCGCGGGCGCA

GCCGCGCCGGCCGCCGCGTCGGGTGCGAAACCCGTGGCAG

CCGCCGCCCGGCCCGCGCAGGTCGCGGCCGCCGGTGCCGC

CGGCGTGCCGGCCGCACGG

Formula (VII) [SEQ ID NO: 12]:

ATGTCAGCCTCCTCCCCCCTCTCCCCGACCGCCGGCGGTC

CGTTCGCGGCCTGGTATGCCGCGTTCGGCGACTGGGCCCG

CACCGACGGCGCCGCGTGGCTCTACCTGTTCAAGGCACTG

CTCGCGGCCTTCATCGCGCTCGGCGTGTCGATGCGGCTCG

ACCTGCCGGCGCCGAAAACGGCAATGACGACCGTCTTCAT

CGTGATGCAGCGCAAAGCGGCGCCGTGCTCGCGAAAAGCT

TCTACCGGGTCGCCGGCACGATCTTCGGGCTCATCGCGAC

GCTCACGTTCGTCGGGCTGTTCCCGCAGCAGCCGCAGCTG

TTCCTGCTGGCGATCGCCCTGTGGATCGCGCTGTGCACCG

CCGGCGCCGCGCGCAACCGCAACTTCCGCAGTTACGGCTT

CCTGCTCGCCGGCTATACGACCGCGC

Formula (VIII) [SEQ ID NO: 13]:

ATGAGCGCGATGACGCGGGTCTCCGAAGTCATCATCGGGA

TCGTGTCGGCCGGCGTCGTCAGCGCGCTCGTGTTTCCTCG

GTACACGGGCGAGCAGATGCGCACGACGGTGCGCAAGCGC

TTCGGCAGCTTCGTCGACTACGTCGCGTCGGCGCTGTCGG

GCCAGCTCGACCGCGCGCACATCGAGACCATCCATACGCG

-continued
CTTCGCCTACGTGGTCGGCTTCGAGGCCGCGCGCAGCATG

GCCGTGTTCGAGGATCCGGACACGCGCATGCGCAGCGGCC

GCCTCGCGCGGCTGAACAGCGAGTTCATGAGCGCGTCGAG

CCGCTTTCACGCGCTGCACCAGCTGATGAACCGGCTGCAC

GCGGCCGGCGCGCAGGCCGCGATCGATGCGATCGAGCCGT

ATTTCCGCGAGATCGCGCCGCTGCTCACGCGCAATGGCGA

ACCCGTGCGCACGTCGATCGACGCCGCGCACTCGGCCGAG

CAACTGCTCGCGTGGCGCGACGCGCTGCCGCGCCGTATCC

GCGCGACACGCGCGGAACTCGAAACGCAGCCCGACTTCCC

GCTGCTCGACTTCGATACCGCCGCCGAACTGCTGTACCGC

TTCATCACCGACCTGCAGGAATACGCGGCGACCTATGCGT

CGCTCGCGACCGCGACGCACGAGCGCGAACGCTGGATCGA

ACGCTACGAGCCGCGCACCAACAAAACGGCCGCCACGATC

GCGGGGATCCGCACCGCGACGGTGATTCTCGCGCTCGGCT

GGTTCTGGATCGAGACTGCGTGGCCGAGCGGCGTGATGCT

GGTGCTGAACGCCGCGGCGACCTGCGCGCTCGCGTCGTCG

GCGCCGCGCCCGACCGCGATGGCCGCGCAGATGGGGATGG

GCACGGCGCTGGCCGTCTGCACCGGCTTCCTGCTGACGTT

CGGCATCTACCCGCGGATCGACGGCTTCGTCCTGCTGTGC

GCGGCGCTCGCGCCGTTGCTCGCGATCGGCATCTACATGT

CGCTGAAGCCGAAGCTCGCCGGCTACGGCGGGGCTATC

Formula (IX) [SEQ ID NO: 14]:

ATGAACGACGCGCTCGCGCTCCTGTTGTCGATGCTCGTCT

CGGCGATCGCGTTCGCCGTGCTGTTCCCGCCGACCGCGCC

GTGGCTCAAGAAACGCCTGTTCGCCGACCTGCGTCACCAG

GCCGTCGCGGCCTGCCACGCGCGGCTCGCCGGACTGCGCA

CGCGCTTCGAGAGCGGCGCGCGCGACCTGATGTACCAGGC

GCACACGCTGTCGGCCGACCACCCGACGTGCAGCGCGACG

CCGTGCTGGATGTTCGCGGTGCTCGAAACCGGGAATGCGG

CCATCGACCTGCGCCACGAGCTGGCAACGCTGCCGTCCGA

CCCGCGCTACGCGCCGACGACGCCGTGGCGCCGTGCGATC

GAAACGATGCGCGCCGCGCTGTCGTCGCTGTTCGCGCGGC

CGGACGCCGAACGTTTCGATGCAACGCTCGCCGCGGTAAA

CGATGCGATCGACGCGACCCGGCAGACGCTCGACGCATTC

ACGCCGACGCGCGAGGAACGCCACCGGCTGCAGCGCATCC

TGAGCCATCTGCATTTCGTGCGCACGGCACTGCTCGATCC

CGAATCGCCGCTCGCCGCGCTCAACCGCAACCGCCCCGTG

CGTCCCCAACCAGGAGCCTCGTCA

Formula (X) [SEQ ID NO: 15]:

ATGCAGATCGACCCGTCGCACTACCAGATCGCGGTCGAGC

AGGCGCAGGCCGTCGCCGCCGCCGCGCGGAGCTGCAGATG

-continued

```
CCGACGACGCGGCCGCCGCGCGGATCTCGATGCGCTCGTC
GTGTCGAAGGAAAACCGCGAGAACGCCGCGCACAGTGCGT
CGAGCGCCGATGCACAGTACCAGCAGGCGATCGCCGCGCT
CGATGCGCGAAGCTCAACGCTCGAGCGCAGCCGCGTCGTC
GCGCCGGTCGACGGCTACATCACGAACCTGCAGACGTTCA
AGGGCAACTATGCGGTGGCCGGCCAGGCGAAGCTCGCGAT
CGTCGACAGCCACTCGTTCTGGGTCTACGGCTACTTCGAG
GAAACCAAGCTGCCGCGCGTGAAGATCGGCGCGCCGGCCG
AAATGCGGCTGATGAGCGGCGGCGTGATGAAGGGCCATGT
CGAAAGCATCTCGCGCGGCATCTACGATCGCGACAACCCG
CAAAGCCGCGACCTCGTCCGGACG
```

(Amino acid sequence)

Formula (I) [SEQ ID NO: 2]:

MARVARSAELPQINGNLSLMRQHWPDNVYYGPGPLANTDT
WNNTGTLGLSYHLDLWGKDKNATERALDTAHATAADARAA
KLELEVNVVRAYVGMSMNYALLDLAHETFERQRSLADLAR
KRLQAGLGTQLEVSQAESTLPDYERQIDSYEEAIQLARHQ
LAALAGKGPGAGDAIKRPRLSLDAPAGLPSAMPADLLGRR
PDVVAARWTVDAQARGIDVAKASFYPNIDLLATVGGFGVT
APFTDFLRAMNGGWTAGPALSLPIFEGGRLRAQLGAANAG
VRPGGRAIQPDDRRRAQGHRRPGRADPFARYAEEGRRTLG
GRQRPQLPAVARRLPPRPDRLRQRAGRAAAIVGAHRKRPP
HRSERLAAHAQLMAALGGGVETGTDVPGSQSSHGESAAGA
AAPAAASGAKPVAAAARPAQVAAAGAAGVPAAR

Formula (II) [SEQ ID NO: 3]:

MSASSPLSPTAGGPFAAWYAAFGDWARTDGAAWLYLFKAL
LAAFIALGVSMRLDLPAPKTAMTTVFIVMQRKAAPCSRKA
STGSPARSSGSSRRSRSSGCSRSSRSCSCWRSPCGSRCAP
PAPRATATSAVTASCSPAIRPR

Formula (III) [SEQ ID NO: 4]:

MSAMTRVSEVIIGIVSAGVVSALVFPRYTGEQMRTTVRKR
FGSFVDYVASALSGQLDRAHIETIHTRFAYVVGFEAARSM
AVFEDPDTRMRSGRLARLNSEFMSASSRFHALHQLMNRLH
AAGAQAAIDAIEPYFREIAPLLTRNGEPVRTSIDAAHSAE
QLLAWRDALPRRIRATRAELETQPDFPLLDFDTAAELLYR
FITDLQEYAATYASLATATHERERWIERYEPRTNKTAATI
AGIRTATVILALGWFWIETAWPSGVMLVLNAAATCALASS
APRPTAMAAQMGMGTALAVCTGFLLTFGIYPRIDGFVLLC
AALAPLLAIGIYMSLKPKLAGYGGAI

Formula (IV) [SEQ ID NO: 5]:

MNDALALLLSMLVSAIAFAVLFPPTAPWLKKRLFADLRHQ

-continued

AVAACHARLAGLRTRFESGARDLMYQAHTLSADHPTCSAT

PCWMFAVLETGNAAIDLRHELATLPSDPRYAPTTPWRRAI

ETMRAALSSLFARPDAERFDATLAAVNDAIDATRQTLDAF

TPTREERHRLQRILSHLHFVRTALLDPESPLAALNRNRPV

RPQPGASS

Formula (V) [SEQ ID NO: 6]:

MQIDPSHYQIAVEQAQAVAAAARSCRCRRRGRRADLDALV

VSKENRENAAHSASSADAQYQQAIAALDARSSTLERSRVV

APVDGYITNLQTFKGNYAVAGQAKLAIVDSHSFWVYGYFE

ETKLPRVKIGAPAEMRLMSGGVMKGHVESISRGIYDRDNP

QSRDLVRT wherein the individual alphabetic letters represent the following amino acids:
A: alanine, C: cysteine, D: aspartic acid,
E: glutamic acid, F: phenylalanine, G: glycine,
H: histidine, I: isoleucine, K: lysine,
L: leucine, M: methionine, N: asparagine,
P: proline, Q: glutamine, R: arginine, S: serine,
T: threonine, V: valine, W: tryptophan, and
Y: tyrosine.

Based on the thus-obtained gene capable of participating in the decomposition or detoxification of fusaric acid and its structure, a plant cell having fusaric acid resistance can be obtained by inserting the above gene between a promoter and a terminator, said promoter and terminator functioning in a plant cell, to transform the latter plant cell. A fusaric acid resistant plant can then be obtained by allowing the above-transformed plant cell to grow to the plant. Since the fusaric acid resistant plant obtained in the manner described above is resistant to diseases caused by fungi of the genus Fusarium, the above method can be used as a control method effective against wilting disease and the like caused by such fungi of the genus Fusarium although their control has heretofore been very difficult. Further, plant cells each of which has been transformed by the gene capable of participating in the decomposition or detoxification of fusaric acid are resistant to fusaric acid, so that they can be used as selective markers. Plant cells can be transformed by a known method, for example, by the method making use of a Ti plasmid ["Zoku Seikagaku Jikken Koza 1, Idenshi Kenkyuho II (Supplemental Handbook of Biochemical Experiments, Vol. 1—Gene Studying Methods II)", pp 205, compiled by Biochemical Society of Japan, Tokyo Kagaku Dojin (1986)] or by the direct gene introduction method (ibid., pp 211).

The identification of the structure of the fusaric acid resistant gene has led to the identification of the protein which can participate in decomposing or detoxifying fusaric acid. Mass production of the protein by a genetic engineering technique can contribute to the control of wilting disease and the like caused by fungi of the genus Fusarium.

The present invention will hereinafter be described in further detail by the following examples. It is however to be noted that the present invention is not limited to or by the following examples.

EXAMPLE 1

Preparation of gene libraries

From the Pseudomonas cepasia UK-1 strain, its DNA was isolated in toto. As an isolation method for the bacterial DNA, the Saito-Miura method can be mentioned by way of example [Saito, H. and Miura, K., Biochim. Biophys. Acta, 72, 619 (1963)]. The DNA so isolated was cleaved by the restriction endonuclease EcoRI and the resulting fragments were fractionated by agarose gel electrophoresis, whereby DNA fragments of 4 kb or greater were collected. Those DNA fragments were inserted in the vector pUC19 which was cleaved by EcoRI and treated with phosphatase. Escherichia coli JM109 was then transformed by plasmids obtained in the manner described above, whereby a gene library of Pseudomonas cepasia was prepared as ampicillin resistant transformants.

With respect to the Klebsiella oxytoca HY-1 strain, a gene library was also prepared by a method similar to the one described above except that DNA fragments cleaved by the endonuclease BamHI/HindIII were inserted in the vector pUC19.

EXAMPLE 2

Screening of gene libraries

A colony of each of the above gene libraries, said colony having been formed on LB medium containing 50 µg/ml of ampicillin, was subjected to replica plating on a secondary selective medium (Davis' minimum agar containing 50 µg/ml of ampicillin, 1 mM of IPTG and 100 µg/ml of fusaric acid), so that a fusaric acid resistant clone was selected.

A clone having the plasmid pBE1 was selected from the gene library of Pseudomonas cepasia. pBE1 contained an EcoRI fragment of 8.5 kb derived from Pseudomonas cepasia. The Escherichia coli strain JM109 containing pBE1 was named "Escherichia coli SAM 1552" and was deposited under the deposit number FERM BP-3285 with Fermentation Research Institute, Agency of Industrial Science and Technology, Ministry of Industrial Trade and Technology, Government of Japan.

On the other hand, a clone having the plasmid pFAR1 was selected from the gene library of Klebsiella oxytoca. pFAR1 contained a BamH/Hind III fragment of 3.6 kb derived from Klebsiella oxytoca. The strain JM109 containing pFAR1 was named "Escherichia coli SAM 1553" and was deposited under the deposit number FERM BP-3286 with Fermentation Research Institute, Agency of Industrial Science and Technology, Ministry of Industrial Trade and Technology, Government of Japan.

EXAMPLE 3

Restriction maps

The plasmids pBE1 and pFAR1 were separately cleaved by various endonucleases. The sizes of the resultant DNA fragments were measured by agarose gel electrophoresis, whereby their restriction maps were prepared. The restriction maps of the DNA fragments inserted in the above plasmids are shown in FIG. 1.

In view of the fact that an *Escherichia coli* strain having pBE1 I with the DNA fragment of 8.5 kb inserted in a direction opposite to the direction of its insertion in pBE1 showed no fusaric acid resistance and, even in the case of an *Escherichia coli* strain having pBE1 , no fusaric acid resistance was exhibited in the absence of IPTG, it has been found that the fusaric acid decomposing or detoxifying gene is expressed under the control of lac promoter present on the vector pUC 19 and its transcription and coding direction runs from the left to the right as viewed in FIG. 1. On the other hand, because a clone having pFAR2 with the DNA fragment of 3.6 kb [SEQ ID NO: 7] inserted in a direction opposite to the direction of its insertion in pFAR1 also has fusaric acid resistance, the fusaric acid decomposing or detoxifying gene is believed to be expressed under the control of a promoter derived from *Klebsiella oxytoca* , said promoter being present on the inserted DNA fragment of 3.6 kb [SEQ ID NO: 7].

EXAMPLE 4

Sub-cloning—Mapping of fusaric acid resistant genes

The position of each fusaric acid resistant gene was determined more specifically by preparing a variety of deleted plasmids on the basis of the corresponding restriction map and investigating the fusaric acid resistance of *Escherichia coli* strains transformed by the deleted plasmids, respectively. Based on the results, subcloning of the fusaric acid resistant genes was conducted.

Figure 2:
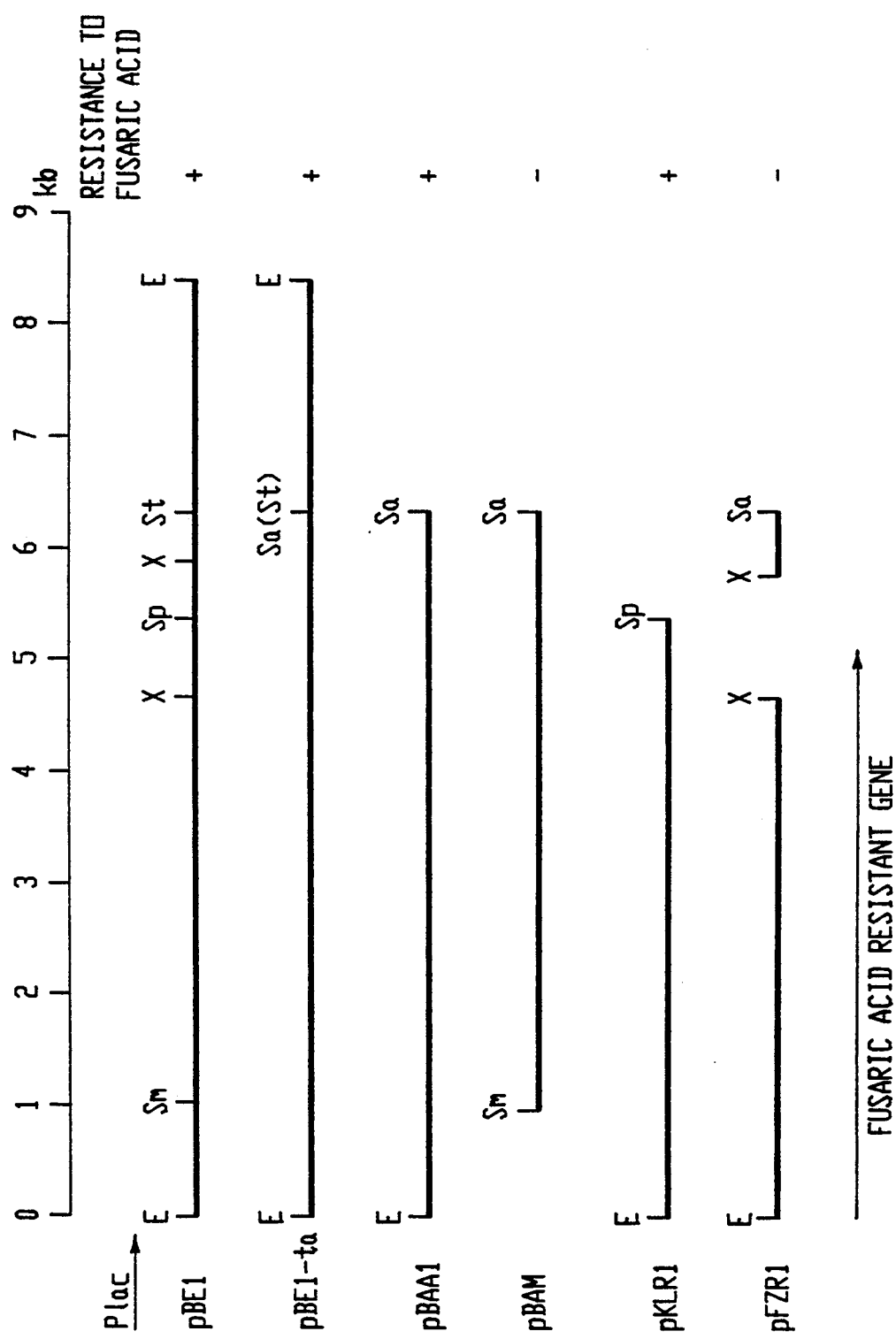
FIG. 2 illustrates a minimum region of the fusaric acid resistant gene derived from Pseudomonas cepasia. In the drawing, the thick lines indicate DNA fragments in which the deleted mutant plasmids shown on the left side have been inserted, respectively, and the fusaric acid resistance of recombinant strains of Escherichia coli, said recombinant strains having been transformed by the plasmids, respectively, is given on the right side (+: resistant to fusaric acid, —: not resistant to fusaric acid). The alphabet letters above the thick lines indicate cleavage sites for the endonucleases (E: EcoRI, Sa: SacI, Sm: SmaI, Sp: SphI, St: StuI, X: XhoI). Sa (St) indicates that an SacI linker has been inserted after cleaving the corresponding DNA fragments with the endonuclease StuI. The arrow on the left side shows the position and direction of the promoter (Plac) which exists on the vector pUC19. The arrow on the bottom end indicates the minimum region of each fusaric acid resistant genes and the direction of transcription.

FIG. 2 shows the deleted plasmids of the plasmid pBE1 having the EcoRI fragment of 8.5 kb derived from *Pseudomonas cepasia* and the fusaric acid resistance of the recombinants obtained by the transformation of *Escherichia coli* JM109 with these deleted plasmids. Since the *Escherichia coli* strain transformed by pBE1 had been found capable of growing in a culture medium containing 500 μg/ml of fusaric acid, the fusaric acid resistance of each strain was then tested by allowing the strain to grow in Davis' minimal medium which contained 500 μg/ml of fusaric acid in addition to 50 μg/ml of ampicillin and 1 mM of IPTG.

The EcoRI fragment which had been inserted in the plasmid pBE1 and is shown in FIG. 1 was cleaved at the StuI site present only near 6.4 kb and an SacI linker (5'-CGAGCTCG-3') was inserted there, whereby a plasmid pBE-ta with the downstream reading frames shifted was prepared. An SacI fragment of 6.4 kb formed by cleaving the plasmid pBE-ta at SacI was inserted to the SacI site of the vector pUC19. The resultant plasmid was named "pBAA1". A further plasmid pBAM was next prepared by deleting a region of the plasmid pBAA1, said region extending from the SmaI site contained in the multi-cloning site of the vector pUC19 (the left end) to the SmaI site at 1 kb. *Escherichia coli* JM109 was transformed by those plasmids and the fusaric acid resistance of the resultant transformants was investigated. The transformants by the plasmids pBE1 -ta and pBAA1 showed fusaric acid resistance but the transformant by the plasmid pBAM did not exhibit fusaric acid resistance.

In addition, various deleted plasmids were also prepared using several SphI sites present in the plasmid pBAA1. After pBAA1 was partially digested by the endonuclease SphI, the resultant fragments were ligated again by T4 ligase. Using the plasmids so obtained, *Escherichia coli* JM109 Was transformed. From the clone showing fusaric acid resistance, the plasmid was prepared, and its restriction map was investigated. A plasmid pKLR1 was found, which was different from the plasmid pBAA1 in that the SphI fragment of about 1.0 kb present on a right-hand side of the plasmid pBAA1 (see FIG. 2) had been deleted. The plasmid pBAA1 was then partly digested by an endonuclease XhoI and the resultant fragments were re-ligated, whereby a plasmid pFZR1 was obtained. The plasmid pFZR1 was different from the plasmid pBAA1 in that a right-hand region of about 1.3 kb had been deleted. A recombinant strain of *Escherichia coli* JM109, said strain having been transformed by pFZR1, showed no fusaric acid resistance.

It has been found from the foregoing results that, in the EcoRI segment of 8.5 kb derived from *Pseudomonas cepasia,* the region extending from the EcoRI site on the left end to the SphI site at 5.4 kb is an essential region for the exhibition of fusaric acid resistance (see FIG. 2).

EXAMPLE 5

Determination of base sequence

Figure 3:
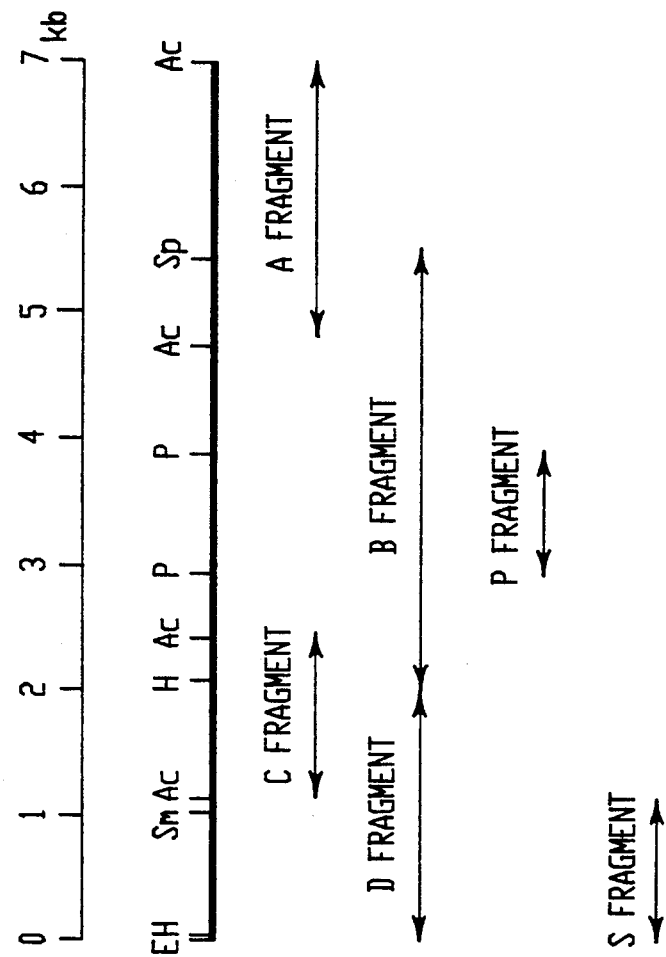
FIG. 3 shows the approach employed upon determination of the base sequence of the DNA which contained the fusaric acid resistant genes derived from Pseudomonas cepasia. In the drawing, the thick line indicates a DNA section whose base sequence was determined. The alphabet letters above the thick line indicate cleavage sites for endonucleases employed for the preparation of various DNA fragments (Ac: AccI, E: EcoRI, H: HindIII, P: PstI, Sm: SmaI, Sp: SphI). The line segments which have at opposite ends thereof arrows pointed in opposite directions indicate the various DNA fragments so prepared.

The base sequence of the DNA fragment coding the fusaric acid resistant gene derived from *Pseudomonas cepasia* was determined. The region whose base sequence was determined was about 7.0 kb long, extending from the EcoRI site to the AccI site of the EcoRI fragment of 8.5 kb in the plasmid pBE1 (see FIG. 3). This region is coding the fusaric acid resistant genes described in Example 3. To determine the base sequence, the EcoRI/AccI fragment of 7.0 kb was first cleaved by various endonucleases on the basis of the restriction map shown in FIG. 1. The resulting DNA fragments were cloned to the phage M13. Here, the individual DNA fragments are mutually overlapped as illustrated in FIG. 3. The phage M13 cloned with the individual fragments was infected to *Escherichia coli* JM 109, whereby double-stranded phage DNAs were prepared.

Those double-stranded phage DNAs were treated with *Escherichia coli* exonuclease III, so that doubles-tranded phage DNAs with a deletion introduced in one direction were prepared. Regarding the preparation method of a plasmid with a deletion introduced in one direction which method makes use of exonuclease III, a detailed description is found at pages 289–305 of "Zoku Seikagaku Jikken Koza 1, Idenshi Kenkyuho II (Supplemental Handbook of Biochemical Experiments, Vol. 1 Gene Studying Methods II)". *Escherichia coli* JM109 was transformed by the individual double-stranded phage DNAs with a deletion introduced in one direction, said DNAs having been obtained by the method described above, whereby phage clones with a deletion inserted in one direction were prepared. A double-stranded phage DNA was prepared from each phage clone. The degree of the deletion was investigated from a cleavage pattern by restriction endonucleases. From suitable clones, single-stranded phage DNAs were prepared. Using those single-stranded phage DNAs as templates, the base sequence of the inserted DNA fragments was determined by the dideoxy technique [Sanger, F., et al., Proc. Natl. Acad. Sci. USA, 74, 5463 (1977)]. The base sequence of each DNA fragment shown in FIG. 3 was determined by uniting the base sequences of DNA fragments inserted in deleted phage clones. The base sequences of the individual DNA fragments shown in FIG. 3 were then united together, whereby the base sequence of the entire EcoRI/AccI fragment of 7.0 kb was determined.

Also determined was the base sequence of the DNA fragment coding the fusaric acid resistant gene derived from *Klebsiella oxytoca*. The section whose base sequence [SEQ ID NO. 7] had been determined was 3.6 kb long, extending from BamHI to HindIII of plasmid pFAR1 (see FIG. 1). As in the case of the above-described fusaric acid resistant gene derived from *Pseudomonas cepacia*, the entire base sequence of the DNA fragment of 3.6 kb [SEQ ID NO: 7] was determined by ascertaining the base sequence of single-stranded phages, in which a deletion had been introduced in one direction, and then connecting them.

EXAMPLE 6

Analysis of base sequence

The EcoRI/AccI fragment of 7.0 kb derived from *Pseudomonas cepacia* consists of 7006 base pairs. Of these base pairs, the entire base sequence (5437 base pairs) of the smallest region which extends from EcoRI to SphI and shows fusaric acid resistance is shown in FIG. 4.

As regions capable of coding proteins in the base sequence [SEQ ID NO: 1], open reading frames (ORF) starting at an initiator codon (ATG or GTG) and ending at a terminator codon (TAA, TAG or TGA) were searched for. Such ORFs were assumed to be directed from the left to the right in FIG. 5, because the transformant having the plasmid pBE11 which was similar to the plasmid pBE1 except for the insertion of the EcoRI fragment of 8.5 kb in the opposite direction did not show fusaric acid resistance. As ORFs consisting of 250 base pairs or more, ten ORFs were found (see FIG. 5). Of these ORFs, especially among ORFs having the SD sequence, which can bind with a ribosome [Shine, J. and Dalgarno, L., Nature, 254, 34–38 (1975)], immediately before the initiator codon ATG and not overlapping with one another, five ORFs, namely, ORF3-1;531→1830 (this indicates starting at the initiator codon ATG of the 531th base pair and ending at the terminator of the 1830th base pair; this definition will be applied equally hereinafter), ORF2-2;1847→2273, ORF1-2;2314→3352, ORF3-2; 3414→4038 and ORF3-3;4473→4977 were estimated as ORFs of a protein having bearing on fusaric acid resistance.

Further, an inverted repeat structure having stable hairpin loops and capable of functioning as a terminator for transcription is observed between the 5125th base pair and the 5157th base pair.

The entire base sequence of the DNA fragment of 3.6 kb derived from *Klebsiella oxytoca* is shown in FIG. 7 [SEQ ID NO: 7]. In the base sequence, open reading frames (ORFs) starting at an initiator codon (ATG or GTG) and ending at a terminator codon (TAA, TAG or TGA) were searched for as regions capable of coding proteins. As ORFs of 300 base pairs or longer, seven ORFs were found in both the directions in total.

EXAMPLE 7

Confirmation of open reading frames

Figure 5:
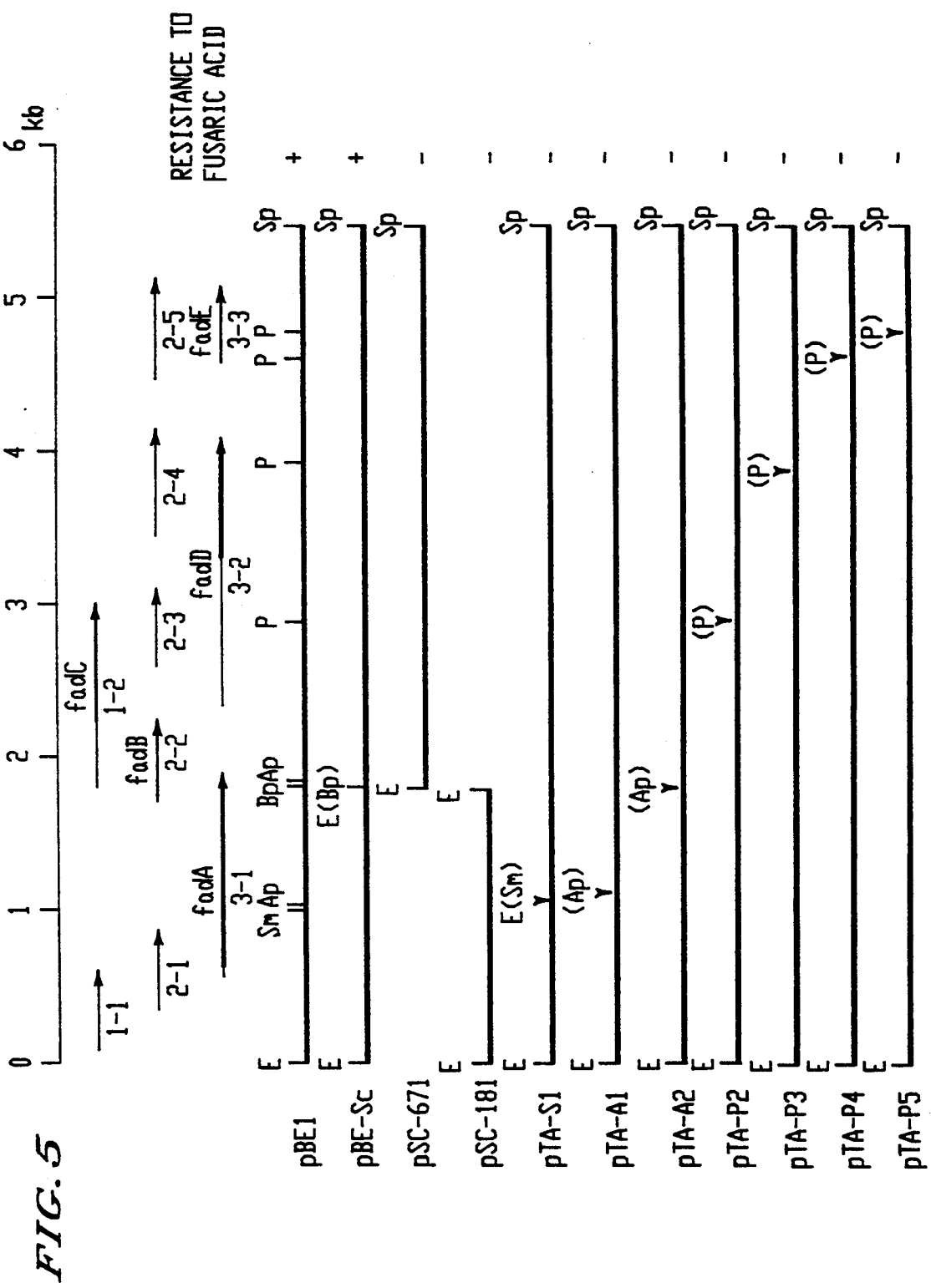

It was confirmed by the following method if the ORFs of *Pseudomonas cepacia* described in Example 6 were actually coding a protein having bearing on fusaric acid resistance. From the base sequence determined above, a detailed restriction map was prepared. After the plasmid pBE1 and the like were cleaved at suitable endonuclease sites, the resultant fragments were treated with Klenow enzyme to form blunt ends. Those fragments were then re-ligated, whereby mutant plasmids with their reading frames shifted after the cleaved sites were prepared. *Escherichia coli* JM109 were transformed with those mutant plasmids. By checking the fusaric acid resistance of the resultant transformants, it was investigated whether or not the ORFs present at the mutation-introduced sites were necessary for fusaric acid resistance. The results are shown in FIG. 5.

In the EcoRI fragment of 8.5 kb inserted in the plasmid pBE1, there is only one cleavage site (1828; this indicates the number of the base pair at the cleavage site) for the endonuclease BstPI. After pBE1 was cleaved by the endonuclease BstPI, the ends of the resultant fragments were converted by Klenow enzyme to blunt ends. Those fragments were re-ligated together by EcoRI linker (5'-GGAATTCC-3'), so that a plasmid pBE1 -sc with the linker incorporated therein was formed. The plasmid pBE1 -sc was cleaved by EcoRI to obtain EcoRI fragments of 1.8 kb and 6.7 kb, respectively. Those fragments were separately inserted in the vector pUC19, whereby plasmids pSC-181 and pSC-671 were prepared.

In the EcoRI fragment of 8.5 kb inserted in the plasmid pBE1, there is also only one cleavage site (1034) for the endonuclease SmaI. Since there is another SmaI site in the multi-cloning site of the vector pUC19, pBE1 -ta was partly digested by SmaI. The resultant fragments were fractionated by electrophoresis to collect DNA molecules in each of which pBE1 was in a linear form. Those linear DNA molecules and the EcoRI linker (5'-GGAATTCC-3') were mixed and ligated by T4 ligase. *Escherichia coli* JM109 was transformed by the resultant plasmids. The plasmids were collected from their corresponding transformants and then cleaved by endonucleases for their analysis. The plasmid containing the EcoRI linker inserted at the SmaI site of the 1036th base pair was named "pTA-Sl".

The DNA fragment inserted in the plasmid pBE1 contains two ApaI sites (1031, 1920). The plasmid pBE1 ta was partly digested by the endonuclease ApaI, and the resultant linear DNA molecules were collected in the same manner as described above. After the cleaved ends of the DNA molecules were converted to blunt ends by Klenow enzyme, those DNA molecules were re-ligated by T4 ligase, whereby mutant plasmids with the downstream reading frames shifted were prepared. The plasmid in which the linker was inserted at the ApaI site of the 1031th base pair and its downstream reading frames were shifted was named "pTA-Al", while the plasmid in which the linker was inserted at the ApaI site of the 1920th base pair and its downstream reading frames were shifted was named "pTA-A2".

There are five cleavage sites (897, 2926, 3921, 4544, 4740) for the endonuclease PstI in the inserted DNA. Using these PstI sites, mutant plasmids pTA P2(2926), pTA-P3(3921), pTA-P4(4544) and pTA-P5(4740) in which the reading frames were shifted were prepared by the above-described method (note: the parenthesized numbers indicate the base pair numbers at the sites downstream of which the reading frames were shifted.). In each of those plasmids, the individual ORFs in the inserted fragment were inserted in the same direction as in the lac promoter of the vector pUC19. The fusaric acid resistance of recombinant strains of *Escherichia coli*, said recombinant strains having been transformed by the mutant plasmids prepared as described above, was investigated. Although the recombinant strain of *Escherichia coli* transformed by the plasmid pBE1-sc was resistant to fusaric acid, the recombinant strains of *Escherichia coli* transformed by the other plasmids (pSC181, pSC671, pTA-S1, pTA-A1, pTA-A2, pTA-P2, pTA-P3, pTA-P4 and pTA-P5) did not show fusaric acid resistance (see FIG. 5).

Since no fusaric acid resistance was exhibited when the EcoRI linker was inserted at the endonuclease SmaI site (1034) or at the ApaI site (1031) and its downstream reading frames were shifted, it has been found that ORF1-1(301→586) and ORF2-1 (368→959) have no bearing on fusaric acid resistance but ORF3-1(459→1837) do have bearing on fusaric acid resistance (the parenthesized numbers appearing after each ORF indicate the base pair numbers of the translation initiator codon and terminator codon, respectively, and the parenthesized number following each endonuclease indicates the base pair number at the cleavage site.). ORF3-1 contains four initiator codons ATG upstream of the cleavage site (1031) for SmaI. Of these, the ATG(531) immediately before which the SD sequence was observed was estimated as an initiator codon and the gene coding that ORF was named "fadA" (see FIG. 5).

The endonuclease BstPI (1828) cleaves immediately after the terminator codon (1830) of ORF3-1 and immediately before the initiator codon (1847) of ORF2-2. Fusaric acid resistance was however retained when the EcoRI linker was introduced at the BstPI site and its downstream reading frames were shifted. Further, no fusaric acid resistance was exhibited when the EcoRI linker was introduced at both the ApaI site (1920) and the PstI site (2926) and their downstream reading frames were shifted. It has hence become clear that ATG(2314) in ORF1-2 (1708→3352) and ORF2-2 are indispensable for fusaric acid resistance. The genes coding those ORFs were named "fadB(1847→273)" and "fadC(2314→3352)", respectively (see FIG. 5). In each of fadB and fadC, the SD sequence is observed immediately before its initiator codon. In view of the fact that fusaric acid resistance was not shown when the EcoRI linker was inserted at the PstI sites (3921, 4544, 4740) and their downstream reading frames were shifted and that there was the SD sequence immediately before each initiator codon, fadD(3413→1038) and fadE(4473→4977) were both regarded as regions coding proteins which are indispensable for fusaric acid resistance.

Putting all the above results together, it has become clear that the five proteins are needed for fusaric acid resistance and the genes coding these proteins are fadA, fadB, fadC, fadD and fadE. The amino acid sequence of these proteins [SEQ ID NOS: 2-6] estimated from the base sequence of these genes are shown in FIG. 4. Further, the estimated molecular weights of these proteins were 45.7 kd (kilodaltons), 37.9 kd, 23.0 kd, 18.5 kd and 14.8 kd. These values were very consistent with the molecular weights of in vitro transcription and coding products obtained using a bacterial cell-free extract, which will be described in Example 8.

It was also investigated in a manner similar to that employed above in the case of *Pseudomonas cepacia* which ORF or ORFs actually codes the protein relevant to the fusaric acid resistance among the seven ORFs contained in the DNA fragment of 3.6 kb [SEQ ID NO: 7] derived from *Klebsiella oxytoca*. Namely, based on the plasmid pFAR1, various plasmids with one or more segments deleted and mutant plasmids with one or more reading frames shifted were prepared. By transforming *Escherichia coli* JM109 with the plasmids thus prepared and studying the fusaric acid resistance of the transformants, it was investigated whether or not the ORFs contained in the deleted or mutation-introduced parts are needed for fusaric acid resistance. As a result, it was revealed that three proteins are needed for fusaric acid resistance. Genes fdt1, fdt2 and fdt3 were then ascertained as genes coding those proteins. Immediately before the initiator codon of each of those three genes, there was observed an SD sequence as a binding site for a ribosome. The amino acid sequence of the protein coded by these genes is illustrated in FIG. 7 [SEQ ID NO. 7].

EXAMPLE 8

Analysis of in vitro transcription and translation products

Actual existence of the transcription and translation products of the individual genes, said products having been identified in Example 7, was confirmed by analyzing gene products which were obtained using the bacterial cell-free extract [DeVries, J.K. and Zubay, G., Proc. Natl. Acad. Sci. USA, 57, 267 (1967)]. In vitro transcription and translation reactions were conducted, using a prokaryotic DNA-directed translation kit (product of Amersham International Plc.) and following the instructions given in the kit. Employed as template DNA molecules were the plasmid pBE1-sc capable of showing fusaric acid resistance and the plasmid pAT153 contained in the kit.

Added successively to 2.5 μg of plasmid DNA were 7.5 μl of supplement solution, 3 μl of amino acid solution, 2 μl (1.11 MBq) of L-[35S methionine] and 5 μl of S-30 extract. They were mixed thoroughly, followed by incubation at 37° C. for 1 hour. Methionine chase solution (5 μl) was added. After the resultant mixture was incubated at 37° C. for 5 minutes, the mixture was ice-cooled to terminate the reaction. The reaction mixture (6 μl) was added with an equiamount of a sample buffer of the twofold concentration, followed by treatment at 95° C. for 5 minutes. Thereafter, proteins were fractionated by SDS-polyacrylamide gel electrophoresis. The SDS-polyacrylamide gel electrophoresis was conducted following the method proposed by Laemmli, U.K. et al. in Nature, 227, 680 (1970). The gel concentration was 15%. After the electrophoresis, the gel was dried by a gel drier. The thus-dried gel was subjected to autoradiography, whereby in vitro transcription and coding products were analyzed.

As is shown in FIG. 6, in the case of the transcription and translation products obtained using as a template the plasmid pBE1-ta capable of showing fusaric acid resistance, five bands were observed in addition to a band corresponding to β-lactamase formed when the control plasmid pAT153 was used as a template. The molecular weights of proteins corresponding to those five bands were estimated on the basis of the migration distance of a molecular weight marker which was concurrently subjected to the electrophoresis. Their molecular weights were estimated to be 47 kd, 38 kd, 23 kd, 18.5 kd and 15 kd, respectively. Those molecular weights were in good conformity with the estimated molecular weights of the proteins coded respectively by the five genes fadA, fadC, fadD, fadE and fadB having bearing on fusaric acid resistance, the latter molecular weights having been described in Example 7. It has been found from the above results that the above five fusaric acid resistant genes are expressed in a recombinant strain of *Escherichia coli*, said recombinant strain having been obtained by transforming *Escherichia coli* with the fusaric acid resistant genes derived from *Pseudomonas cepasia*, and has made *Escherichia coli* resistant to fusaric acid.

We claim:

1. An isolated and purified DNA consisting essentially of a sequence encoding amino acid sequences which decompose or detoxify fusaric acid, said amino acid sequences being SEQ ID NOS: 2-6.

2. The isolated and purified DNA of claim 1, wherein said DNA is isolated from *Pseudomonas cepacia*.

3. A process for the production of proteins of SEQ ID NOS: 2-6, comprising:
    transforming a host *Escherichia coli* cell with a plasmid containing a DNA sequence encoding said proteins;
    culturing said transformed cell in a suitable medium; and purifying and isolating said proteins.

4. An isolated and purified DNA consisting essentially of a sequence encoding amino acid sequences which decompose or detoxify fusaric acid, said amino acid sequences being SEQ ID NOS: 8-10.

5. The isolated and purified DNA of claim 4, said DNA being isolated from *Klebsiella oxytoca*.

6. The isolated and purified DNA of claim 4, wherein said DNA is isolated from *Escherichia coli* SAM 1553.

7. A process for the production of proteins of SEQ ID NOS: 8-10, comprising:
    transforming a host *Escherichia coli* cell with a plasmid containing a DNA sequence encoding said proteins,
    culturing said transformed cell in a suitable medium; and
    purifying and isolating said proteins.

8. The process of claim 7, said DNA being isolated from *Klebsiella oxytoca*.

9. The process of claim 7, wherein said DNA is isolated from *Escherichia coli* SAM 1553.

10. A plasmid comprising the DNA of claim 1, 2, 4, 6 or 5.

11. A host *Escherichia coli* cell comprising the plasmid of claim 10.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 5437 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: Pseudomonas cepacia ( i x ) FEATURE:
        ( A ) NAME/KEY: RBS
        ( B ) LOCATION: 519..522

( i x ) FEATURE:
        ( A ) NAME/KEY: CDS
        ( B ) LOCATION: 531..1832

( i x ) FEATURE:
        ( A ) NAME/KEY: RBS
        ( B ) LOCATION: 1836..1839

( i x ) FEATURE:
        ( A ) NAME/KEY: CDS
        ( B ) LOCATION: 1847..2275

( i x ) FEATURE:
        ( A ) NAME/KEY: RBS
        ( B ) LOCATION: 2301..2304

( i x ) FEATURE:
        ( A ) NAME/KEY: CDS
        ( B ) LOCATION: 2314..3354

( i x ) FEATURE:
        ( A ) NAME/KEY: RBS
        ( B ) LOCATION: 3405..3409

( i x ) FEATURE:
        ( A ) NAME/KEY: CDS
        ( B ) LOCATION: 3414..4040

( i x ) FEATURE:
        ( A ) NAME/KEY: RBS
        ( B ) LOCATION: 4457..4462

( i x ) FEATURE:
        ( A ) NAME/KEY: CDS
        ( B ) LOCATION: 4473..4979

( x i ) SEQUENCE DESCRIPTION: SEQ ID NO:1:

```
GAATTCATCT  GCTGGGCGGC  CGCGGTAAAG  CTTCCCGCGT  CGACCACGCG  GACGAATACC           60

CGCATGTTTT  GTAACGTATC  CATCCCATTA  CCCGTTTGAA  TCCGGACGGA  TTGTTGCACA          120

GAGGCAAACA  AGTATTGTCT  CAGGATTCGT  AAAAATGACT  TGCACCCTTG  TCCATATATT          180
```

| | | | | | | | | | | | |
|---|---|---|---|---|---|---|---|---|---|---|---|
|CAGGAATCGC|TGAAAAATAT|AATCGCATCC|GACTCATCTA|TATCCGAAAG|GGAGAAAATC| | | | | |240|
|GTGCAGTCTC|CGGCGACAAA|AGGGACGCTC|GCACTGGCGG|TTCTTGCAGT|CTCATTAATA| | | | | |300|
|ATGGCCGGGT|GCGCGAGCAT|GGGCGACAAC|AAGCCGCAGT|CGGCCCGCAT|CGAAGCGAAC| | | | | |360|
|GCGCTCGATG|CCGGCGCGGC|CATCCGCGCG|GCCGACCGCG|ACGCGGGCTG|GCCCGCGGCC| | | | | |420|
|GACTGGTGGC|GCGCCTACCG|CGATCCGCAA|CTCGACACAT|GGATTGCCGC|CGCGCAGGCC| | | | | |480|
|GGCAACCCGA|CGCTCGCGGC|CGCCGAGGCC|GCGTGCGCGA|AGCGCAGGCG|ATG GCG| | | | | |536|

```
                                                                                    Met Ala
                                                                                      1

CGC GTG GCC CGC TCG GCC GAA TTG CCA CAG ATC AAC GGC AAC CTC TCG                      584
Arg Val Ala Arg Ser Ala Glu Leu Pro Gln Ile Asn Gly Asn Leu Ser
         5                   10                  15

CTG ATG CGC CAG CAC TGG CCG GAC AAC GTC TAT TAC GGC CCC GGC CCG                      632
Leu Met Arg Gln His Trp Pro Asp Asn Val Tyr Tyr Gly Pro Gly Pro
     20                  25                  30

CTC GCG AAC ACC GAC ACC TGG AAC AAC ACC GGC ACG CTC GGC CTG TCC                      680
Leu Ala Asn Thr Asp Thr Trp Asn Asn Thr Gly Thr Leu Gly Leu Ser
 35              40                  45                      50

TAC CAC CTC GAC CTG TGG GGC AAG GAC AAG AAC GCG ACC GAG CGC GCG                      728
Tyr His Leu Asp Leu Trp Gly Lys Asp Lys Asn Ala Thr Glu Arg Ala
             55                  60                      65

CTC GAT ACC GCG CAC GCG ACC GCC GCC GAC GCA CGC GCG GCG AAG CTC                      776
Leu Asp Thr Ala His Ala Thr Ala Ala Asp Ala Arg Ala Ala Lys Leu
         70                  75                  80

GAA CTC GAA GTC AAC GTC GTG CGC GCG TAC GTC GGC ATG TCG ATG AAC                      824
Glu Leu Glu Val Asn Val Val Arg Ala Tyr Val Gly Met Ser Met Asn
             85                  90                  95

TAC GCG CTG CTC GAC CTC GCG CAC GAA ACG TTC GAA CGC CAG CGC TCG                      872
Tyr Ala Leu Leu Asp Leu Ala His Glu Thr Phe Glu Arg Gln Arg Ser
    100                 105                 110

CTC GCC GAT CTC GCG CGC AAG CGG CTG CAG GCT GGC CTC GGC ACG CAG                      920
Leu Ala Asp Leu Ala Arg Lys Arg Leu Gln Ala Gly Leu Gly Thr Gln
115                 120                 125                 130

CTC GAG GTG AGC CAG GCG GAA TCG ACG CTG CCC GAC TAT GAG CGC CAG                      968
Leu Glu Val Ser Gln Ala Glu Ser Thr Leu Pro Asp Tyr Glu Arg Gln
                135                 140                 145

ATC GAC AGC TAC GAG GAA GCG ATC CAG CTC GCG CGG CAC CAG CTC GCC                     1016
Ile Asp Ser Tyr Glu Glu Ala Ile Gln Leu Ala Arg His Gln Leu Ala
            150                 155                 160

GCA CTG GCC GGC AAG GGC CCG GGC GCC GGC GAT GCG ATC AAG CGG CCT                     1064
Ala Leu Ala Gly Lys Gly Pro Gly Ala Gly Asp Ala Ile Lys Arg Pro
        165                 170                 175

CGG CTG TCG CTC GAC GCA CCG GCC GGC TTG CCG TCG GCG ATG CCG GCC                     1112
Arg Leu Ser Leu Asp Ala Pro Ala Gly Leu Pro Ser Ala Met Pro Ala
180                 185                 190

GAC CTG CTC GGC CGC CGC CCC GAC GTC GTC GCG GCA CGC TGG ACG GTC                     1160
Asp Leu Leu Gly Arg Arg Pro Asp Val Val Ala Ala Arg Trp Thr Val
195                 200                 205                 210

GAC GCG CAG GCG CGC GGC ATC GAC GTC GCA AAG GCT TCG TTC TAT CCG                     1208
Asp Ala Gln Ala Arg Gly Ile Asp Val Ala Lys Ala Ser Phe Tyr Pro
                215                 220                 225

AAC ATC GAC CTG CTC GCG ACG GTC GGC GGC TTC GGC GTG ACC GCG CCG                     1256
Asn Ile Asp Leu Leu Ala Thr Val Gly Gly Phe Gly Val Thr Ala Pro
            230                 235                 240

TTC ACC GAC TTC CTG CGC GCG ATG AAC GGC GGC TGG ACG GCC GGC CCC                     1304
Phe Thr Asp Phe Leu Arg Ala Met Asn Gly Gly Trp Thr Ala Gly Pro
        245                 250                 255

GCG CTG TCG CTG CCG ATC TTC GAA GGC GGC CGG CTG CGC GCG CAG CTC                     1352
Ala Leu Ser Leu Pro Ile Phe Glu Gly Gly Arg Leu Arg Ala Gln Leu
260                 265                 270
```

-continued

| | | | | | | | | | | | | | | | |
|---|---|---|---|---|---|---|---|---|---|---|---|---|---|---|---|
| GGC | GCG | GCG | AAT | GCC | GGC | GTA | CGA | CCA | GGC | GGT | CGA | GCA | ATA | CAA | CCA | 1400 |
| Gly | Ala | Ala | Asn | Ala | Gly | Val | Arg | Pro | Gly | Gly | Arg | Ala | Ile | Gln | Pro |
| 275 | | | | 280 | | | | | 285 | | | | | 290 | |

GAC GAT CGT CGG CGC GCT CAA GGA CAT CGC CGA CCA GGT CGT GCG GAT 1448
Asp Asp Arg Arg Arg Ala Gln Gly His Arg Arg Pro Gly Arg Ala Asp
              295                         300                         305

CCG TTC GCT CGA TAC GCA GAA GAA GGA CGC CGC ACG CTC GGT GGC CGC 1496
Pro Phe Ala Arg Tyr Ala Glu Glu Gly Arg Arg Thr Leu Gly Gly Arg
              310                         315                         320

CAA CGA CCG CAG TTA CCA GCT GTC GCG CGA AGG CTT CCG CCG CGG CCT 1544
Gln Arg Pro Gln Leu Pro Ala Val Ala Arg Arg Leu Pro Pro Arg Pro
325                         330                         335

GAC CGA CTA CGT CAA CGT GCT GGT CGC GCA GCA GCA ATT GTT GGC GCG 1592
Asp Arg Leu Arg Gln Arg Ala Gly Arg Ala Ala Ala Ile Val Gly Ala
340                         345                         350

CAC AGG AAA CGG CCG CCG CAT CGA TCG GAA CGC CTC GCC GCG CAC GCT 1640
His Arg Lys Arg Pro Pro His Arg Ser Glu Arg Leu Ala Ala His Ala
355                         360                         365                         370

CAA CTG ATG GCC GCG CTG GGT GGC GGC GTC GAG ACG GGC ACG GAC GTG 1688
Gln Leu Met Ala Ala Leu Gly Gly Gly Val Glu Thr Gly Thr Asp Val
              375                         380                         385

CCG GGC AGC CAA TCG TCG CAT GGC GAA TCC GCC GCG GGC GCA GCC GCG 1736
Pro Gly Ser Gln Ser Ser His Gly Glu Ser Ala Ala Gly Ala Ala Ala
              390                         395                         400

CCG GCC GCC GCG TCG GGT GCG AAA CCC GTG GCA GCC GCC GCC CGG CCC 1784
Pro Ala Ala Ala Ser Gly Ala Lys Pro Val Ala Ala Ala Ala Arg Pro
         405                         410                         415

GCG CAG GTC GCG GCC GCC GGT GCC GCC GGC GTG CCG GCC GCA CGG TAACCCGG 1839
Ala Gln Val Ala Ala Ala Gly Ala Ala Gly Val Pro Ala Ala Arg
420                         425                         430

CGACGCC ATG TCA GCC TCC TCC CCC CTC TCC CCG ACC GCC GGC GGT CCG 1888
         Met Ser Ala Ser Ser Pro Leu Ser Pro Thr Ala Gly Gly Pro
           1           5                         10

TTC GCG GCC TGG TAT GCC GCG TTC GGC GAC TGG GCC CGC ACC GAC GGC 1936
Phe Ala Ala Trp Tyr Ala Ala Phe Gly Asp Trp Ala Arg Thr Asp Gly
15                         20                         25                         30

GCC GCG TGG CTC TAC CTG TTC AAG GCA CTG CTC GCG GCC TTC ATC GCG 1984
Ala Ala Trp Leu Tyr Leu Phe Lys Ala Leu Leu Ala Ala Phe Ile Ala
              35                         40                         45

CTC GGC GTG TCG ATG CGG CTC GAC CTG CCG GCG CCG AAA ACG GCA ATG 2032
Leu Gly Val Ser Met Arg Leu Asp Leu Pro Ala Pro Lys Thr Ala Met
              50                         55                         60

ACG ACC GTC TTC ATC GTG ATG CAG CGC AAA GCG GCG CCG TGC TCG CGA 2080
Thr Thr Val Phe Ile Val Met Gln Arg Lys Ala Ala Pro Cys Ser Arg
         65                         70                         75

AAA GCT TCT ACC GGG TCG CCG GCA CGA TCT TCG GGC TCA TCG CGA CGC 2128
Lys Ala Ser Thr Gly Ser Pro Ala Arg Ser Ser Gly Ser Ser Arg Arg
80                         85                         90

TCA CGT TCG TCG GGC TGT TCC CGC AGC AGC CGC AGC TGT TCC TGC TGG 2176
Ser Arg Ser Ser Gly Cys Ser Arg Ser Ser Arg Ser Cys Ser Cys Trp
95                         100                         105                         110

CGA TCG CCC TGT GGA TCG CGC TGT GCA CCG CCG GCG CCG CGC GCA ACC 2224
Arg Ser Pro Cys Gly Ser Arg Cys Ala Pro Pro Ala Pro Arg Ala Thr
              115                         120                         125

GCA ACT TCC GCA GTT ACG GCT TCC TGC TCG CCG GCT ATA CGA CCG CGC 2272
Ala Thr Ser Ala Val Thr Ala Ser Cys Ser Pro Ala Ile Arg Pro Arg
              130                         135                         140

TGATCGGCCT GCCCGCGTCG CAGCACCCGG ATGGCGCATT C ATG AGC GCG ATG 2325
                                              Met Ser Ala Met
                                                1

| | |
|---|---|
| ACG CGG GTC TCC GAA GTC ATC ATC GGG ATC GTG TCG GCC GGC GTC GTC<br>Thr Arg Val Ser Glu Val Ile Ile Gly Ile Val Ser Ala Gly Val Val<br>5                        10                   15                   20 | 2373 |
| AGC GCG CTC GTG TTT CCT CGG TAC ACG GGC GAG CAG ATG CGC ACG ACG<br>Ser Ala Leu Val Phe Pro Arg Tyr Thr Gly Glu Gln Met Arg Thr Thr<br>               25                   30                  35 | 2421 |
| GTG CGC AAG CGC TTC GGC AGC TTC GTC GAC TAC GTC GCG TCG GCG CTG<br>Val Arg Lys Arg Phe Gly Ser Phe Val Asp Tyr Val Ala Ser Ala Leu<br>          40                   45                 50 | 2469 |
| TCG GGC CAG CTC GAC CGC GCG CAC ATC GAG ACC ATC CAT ACG CGC TTC<br>Ser Gly Gln Leu Asp Arg Ala His Ile Glu Thr Ile His Thr Arg Phe<br>              55                   60                65 | 2517 |
| GCC TAC GTG GTC GGC TTC GAG GCC GCG CGC AGC ATG GCC GTG TTC GAG<br>Ala Tyr Val Val Gly Phe Glu Ala Ala Arg Ser Met Ala Val Phe Glu<br>     70                   75                  80 | 2565 |
| GAT CCG GAC ACG CGC ATG CGC AGC GGC CGC CTC GCG CGG CTG AAC AGC<br>Asp Pro Asp Thr Arg Met Arg Ser Gly Arg Leu Ala Arg Leu Asn Ser<br>85                       90                  95               100 | 2613 |
| GAG TTC ATG AGC GCG TCG AGC CGC TTT CAC GCG CTG CAC CAG CTG ATG<br>Glu Phe Met Ser Ala Ser Ser Arg Phe His Ala Leu His Gln Leu Met<br>              105                110              115 | 2661 |
| AAC CGG CTG CAC GCG GCC GGC GCG CAG GCC GCG ATC GAT GCG ATC GAG<br>Asn Arg Leu His Ala Ala Gly Ala Gln Ala Ala Ile Asp Ala Ile Glu<br>        120                  125                130 | 2709 |
| CCG TAT TTC CGC GAG ATC GCG CCG CTG CTC ACG CGC AAT GGC GAA CCC<br>Pro Tyr Phe Arg Glu Ile Ala Pro Leu Leu Thr Arg Asn Gly Glu Pro<br>            135                  140              145 | 2757 |
| GTG CGC ACG TCG ATC GAC GCC GCG CAC TCG GCC GAG CAA CTG CTC GCG<br>Val Arg Thr Ser Ile Asp Ala Ala His Ser Ala Glu Gln Leu Leu Ala<br>150                     155                160 | 2805 |
| TGG CGC GAC GCG CTG CCG CGC CGT ATC CGC GCG ACA CGC GCG GAA CTC<br>Trp Arg Asp Ala Leu Pro Arg Arg Ile Arg Ala Thr Arg Ala Glu Leu<br>165                     170                175              180 | 2853 |
| GAA ACG CAG CCC GAC TTC CCG CTG CTC GAC TTC GAT ACC GCC GCC GAA<br>Glu Thr Gln Pro Asp Phe Pro Leu Leu Asp Phe Asp Thr Ala Ala Glu<br>              185                190              195 | 2901 |
| CTG CTG TAC CGC TTC ATC ACC GAC CTG CAG GAA TAC GCG GCG ACC TAT<br>Leu Leu Tyr Arg Phe Ile Thr Asp Leu Gln Glu Tyr Ala Ala Thr Tyr<br>        200                  205                210 | 2949 |
| GCG TCG CTC GCG ACC GCG ACG CAC GAG CGC GAA CGC TGG ATC GAA CGC<br>Ala Ser Leu Ala Thr Ala Thr His Glu Arg Glu Arg Trp Ile Glu Arg<br>            215                220              225 | 2997 |
| TAC GAG CCG CGC ACC AAC AAA ACG GCC GCC ACG ATC GCG GGG ATC CGC<br>Tyr Glu Pro Arg Thr Asn Lys Thr Ala Ala Thr Ile Ala Gly Ile Arg<br>230                     235                240 | 3045 |
| ACC GCG ACG GTG ATT CTC GCG CTC GGC TGG TTC TGG ATC GAG ACT GCG<br>Thr Ala Thr Val Ile Leu Ala Leu Gly Trp Phe Trp Ile Glu Thr Ala<br>245                     250                255              260 | 3093 |
| TGG CCG AGC GGC GTG ATG CTG GTG CTG AAC GCC GCG GCG ACC TGC GCG<br>Trp Pro Ser Gly Val Met Leu Val Leu Asn Ala Ala Ala Thr Cys Ala<br>              265                270              275 | 3141 |
| CTC GCG TCG TCG GCG CCG CGC CCG ACC GCG ATG GCC GCG CAG ATG GGG<br>Leu Ala Ser Ser Ala Pro Arg Pro Thr Ala Met Ala Ala Gln Met Gly<br>        280                  285                290 | 3189 |
| ATG GGC ACG GCG CTG GCC GTC TGC ACC GGC TTC CTG CTG ACG TTC GGC<br>Met Gly Thr Ala Leu Ala Val Cys Thr Gly Phe Leu Leu Thr Phe Gly<br>            295                300              305 | 3237 |
| ATC TAC CCG CGG ATC GAC GGC TTC GTC CTG CTG TGC GCG GCG CTC GCG<br>Ile Tyr Pro Arg Ile Asp Gly Phe Val Leu Leu Cys Ala Ala Leu Ala<br>310                     315                320 | 3285 |
| CCG TTG CTC GCG ATC GGC ATC TAC ATG TCG CTG AAG CCG AAG CTC GCC | 3333 |

| | | | | | | | | | | | | | | | |
|---|---|---|---|---|---|---|---|---|---|---|---|---|---|---|---|
|Pro|Leu|Leu|Ala|Ile|Gly|Ile|Tyr|Met|Ser|Leu|Lys|Pro|Lys|Leu|Ala|
|325| | | | |330| | | |335| | | |340| | |

GGC TAC GGC GGG GCT ATC TGATCTTCTT CTGCTTCCTC GCCGGCCCCG 3381
Gly Tyr Gly Gly Ala Ile
                  345

ACAGCATCAC GCACTACGAT CCCACGAGCT TC ATG AAC GAC GCG CTC GCG CTC 3434
                                                      Met Asn Asp Ala Leu Ala Leu
                                                         1            5

CTG TTG TCG ATG CTC GTC TCG GCG ATC GCG TTC GCC GTG CTG TTC CCG 3482
Leu Leu Ser Met Leu Val Ser Ala Ile Ala Phe Ala Val Leu Phe Pro
          10                   15                  20

CCG ACC GCG CCG TGG CTC AAG AAA CGC CTG TTC GCC GAC CTG CGT CAC 3530
Pro Thr Ala Pro Trp Leu Lys Lys Arg Leu Phe Ala Asp Leu Arg His
     25                 30                 35

CAG GCC GTC GCG GCC TGC CAC GCG CGG CTC GCC GGA CTG CGC ACG CGC 3578
Gln Ala Val Ala Ala Cys His Ala Arg Leu Ala Gly Leu Arg Thr Arg
40                 45                   50                55

TTC GAG AGC GGC GCG CGC GAC CTG ATG TAC CAG GCG CAC ACG CTG TCG 3626
Phe Glu Ser Gly Ala Arg Asp Leu Met Tyr Gln Ala His Thr Leu Ser
              60                   65                   70

GCC GAC CAC CCG ACG TGC AGC GCG ACG CCG TGC TGG ATG TTC GCG GTG 3674
Ala Asp His Pro Thr Cys Ser Ala Thr Pro Cys Trp Met Phe Ala Val
          75                   80                   85

CTC GAA ACC GGG AAT GCG GCC ATC GAC CTG CGC CAC GAG CTG GCA ACG 3722
Leu Glu Thr Gly Asn Ala Ala Ile Asp Leu Arg His Glu Leu Ala Thr
            90                   95                  100

CTG CCG TCC GAC CCG CGC TAC GCG CCG ACG ACG CCG TGG CGC CGT GCG 3770
Leu Pro Ser Asp Pro Arg Tyr Ala Pro Thr Thr Pro Trp Arg Arg Ala
105                110                  115

ATC GAA ACG ATG CGC GCC GCG CTG TCG TCG CTG TTC GCG CGG CCG GAC 3818
Ile Glu Thr Met Arg Ala Ala Leu Ser Ser Leu Phe Ala Arg Pro Asp
120                125                130               135

GCC GAA CGT TTC GAT GCA ACG CTC GCC GCG GTA AAC GAT GCG ATC GAC 3866
Ala Glu Arg Phe Asp Ala Thr Leu Ala Ala Val Asn Asp Ala Ile Asp
              140                       145               150

GCG ACC CGG CAG ACG CTC GAC GCA TTC ACG CCG ACG CGC GAG GAA CGC 3914
Ala Thr Arg Gln Thr Leu Asp Ala Phe Thr Pro Thr Arg Glu Glu Arg
                 155                 160                 165

CAC CGG CTG CAG CGC ATC CTG AGC CAT CTG CAT TTC GTG CGC ACG GCA 3962
His Arg Leu Gln Arg Ile Leu Ser His Leu His Phe Val Arg Thr Ala
          170                   175                180

CTG CTC GAT CCC GAA TCG CCG CTC GCC GCG CTC AAC CGC AAC CGC CCC 4010
Leu Leu Asp Pro Glu Ser Pro Leu Ala Ala Leu Asn Arg Asn Arg Pro
185                190                195

GTG CGT CCC CAA CCA GGA GCC TCG TCA TGATGCCGCG TGAAATCGCC 4057
Val Arg Pro Gln Pro Gly Ala Ser Ser
200                205

ATTCTCGATG CCTACATGCC CACGGTGGTG CTGATGTTCG TCCTCGGCGC GCTCGCGACC 4117

TGGGCCGTCG ACCGCCTGCT CGCCTATACG GGCCTCTACC GTCTCGTCTG GCACCCGTCG 4177

CTGTTCCGGG CCTGCCTCCT CGTCTGCATT TGCGGCGGAC TGAGTCTTGC CGTTTACCGT 4237

TGATTCCGAA CCATCATGAG TTCTCAGAAA ACTCTTCGGC TTCGTCGCGA CCGCCGTCAT 4297

TCTTCTCGTC GCGATCCTGA TCGGGCCGCT CGCTGTGGGT GCACTACATG GACGATCCGT 4357

GGACGCGCGA CGGCCGTGCG CGCCGCAGAT CGTCAACGTC GCGCCGGACG TGTCGGGCGC 4417

GATCGTCGAA CTGCCCGTGC ATGACAACCA GCTCGTGAAA AAGGGCGACC TGATC ATG 4475
                                                                                               Met
                                                                                               1

| | | | | | | | | | | | | | | | | |
|---|---|---|---|---|---|---|---|---|---|---|---|---|---|---|---|---|
| CAG | ATC | GAC | CCG | TCG | CAC | TAC | CAG | ATC | GCG | GTC | GAG | CAG | GCG | CAG | GCC | 4523 |
| Gln | Ile | Asp | Pro | Ser | His | Tyr | Gln | Ile | Ala | Val | Glu | Gln | Ala | Gln | Ala | |
| | | | 5 | | | | | 10 | | | | | 15 | | | |
| GTC | GCC | GCC | GCC | GCG | CGG | AGC | TGC | AGA | TGC | CGA | CGA | CGC | GGC | CGC | CGC | 4571 |
| Val | Ala | Ala | Ala | Ala | Arg | Ser | Cys | Arg | Cys | Arg | Arg | Arg | Gly | Arg | Arg | |
| | | | 20 | | | | 25 | | | | | 30 | | | | |
| GCG | GAT | CTC | GAT | GCG | CTC | GTC | GTG | TCG | AAG | GAA | AAC | CGC | GAG | AAC | GCC | 4619 |
| Ala | Asp | Leu | Asp | Ala | Leu | Val | Val | Ser | Lys | Glu | Asn | Arg | Glu | Asn | Ala | |
| | | | 35 | | | | 40 | | | | | 45 | | | | |
| GCG | CAC | AGT | GCG | TCG | AGC | GCC | GAT | GCA | CAG | TAC | CAG | CAG | GCG | ATC | GCC | 4667 |
| Ala | His | Ser | Ala | Ser | Ser | Ala | Asp | Ala | Gln | Tyr | Gln | Gln | Ala | Ile | Ala | |
| 50 | | | | | 55 | | | | | 60 | | | | | 65 | |
| GCG | CTC | GAT | GCG | CGA | AGC | TCA | ACG | CTC | GAG | CGC | AGC | CGC | GTC | GTC | GCG | 4715 |
| Ala | Leu | Asp | Ala | Arg | Ser | Ser | Thr | Leu | Glu | Arg | Ser | Arg | Val | Val | Ala | |
| | | | | 70 | | | | | 75 | | | | | 80 | | |
| CCG | GTC | GAC | GGC | TAC | ATC | ACG | AAC | CTG | CAG | ACG | TTC | AAG | GGC | AAC | TAT | 4763 |
| Pro | Val | Asp | Gly | Tyr | Ile | Thr | Asn | Leu | Gln | Thr | Phe | Lys | Gly | Asn | Tyr | |
| | | | | 85 | | | | | 90 | | | | | 95 | | |
| GCG | GTG | GCC | GGC | CAG | GCG | AAG | CTC | GCG | ATC | GTC | GAC | AGC | CAC | TCG | TTC | 4811 |
| Ala | Val | Ala | Gly | Gln | Ala | Lys | Leu | Ala | Ile | Val | Asp | Ser | His | Ser | Phe | |
| | | | | 100 | | | | | 105 | | | | | 110 | | |
| TGG | GTC | TAC | GGC | TAC | TTC | GAG | GAA | ACC | AAG | CTG | CCG | CGC | GTG | AAG | ATC | 4859 |
| Trp | Val | Tyr | Gly | Tyr | Phe | Glu | Glu | Thr | Lys | Leu | Pro | Arg | Val | Lys | Ile | |
| | | | | 115 | | | | | 120 | | | | | 125 | | |
| GGC | GCG | CCG | GCC | GAA | ATG | CGG | CTG | ATG | AGC | GGC | GGC | GTG | ATG | AAG | GGC | 4907 |
| Gly | Ala | Pro | Ala | Glu | Met | Arg | Leu | Met | Ser | Gly | Gly | Val | Met | Lys | Gly | |
| 130 | | | | | 135 | | | | | 140 | | | | | 145 | |
| CAT | GTC | GAA | AGC | ATC | TCG | CGC | GGC | ATC | TAC | GAT | CGC | GAC | AAC | CCG | CAA | 4955 |
| His | Val | Glu | Ser | Ile | Ser | Arg | Gly | Ile | Tyr | Asp | Arg | Asp | Asn | Pro | Gln | |
| | | | | 150 | | | | | 155 | | | | | 160 | | |
| AGC | CGC | GAC | CTC | GTC | CGG | ACG | TGAACCCGAC | CTTCAACTGG | GTGCGCCTCG | | | | | | | 5006 |
| Ser | Arg | Asp | Leu | Val | Arg | Thr | | | | | | | | | | |
| | | | | 165 | | | | | | | | | | | | |

```
CGCAGCGCGT  GCCGGTGCGC  ATCAGGATCG  ACGAATGGCC  GGCCGACGTG  GTGCTGTCGG     5066

CGGGTACGAC  CTGCACGGTC  ATCATCGATC  CGGACAAGCA  GAAGAAGTCG  TAAGCGCAAC     5126

GCGCGCCGGG  CGGCATCCCG  CCCGGCGGCG  TCACTCCCAG  AAGAACCGGT  AAGGCAGGAA     5186

CGGCGACGGG  CCGAGCCCCG  CTTCGCCGAT  CATGTTGCGC  AACCGCATCG  CAAAGCCGAT     5246

GGCGCCGATC  ACGACGAGTG  CGGCGATCAC  ATACGGGCGC  CGCACGTACG  GCACGCGTTG     5306

CAGCGGCACG  AACTGGCAGC  CCATCGCGAA  CAGCACGAGC  CACTGGAAGC  GCAGCCCCGC     5366

ATAGCTGACC  CGCGCGAGCG  CGAAACTCGC  GATCTCGCAG  GCGAACAGGA  ACACGAGCGT     5426

GCGCGGCATG  C                                                              5437
```

( 2 ) INFORMATION FOR SEQ ID NO:2:

( i ) SEQUENCE CHARACTERISTICS:
       ( A ) LENGTH: 433 amino acids
       ( B ) TYPE: amino acid
       ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Arg | Val | Ala | Arg | Ser | Ala | Glu | Leu | Pro | Gln | Ile | Asn | Gly | Asn |
| 1 | | | | 5 | | | | | 10 | | | | | 15 | |
| Leu | Ser | Leu | Met | Arg | Gln | His | Trp | Pro | Asp | Asn | Val | Tyr | Tyr | Gly | Pro |
| | | | 20 | | | | | 25 | | | | | 30 | | |
| Gly | Pro | Leu | Ala | Asn | Thr | Asp | Thr | Trp | Asn | Asn | Thr | Gly | Thr | Leu | Gly |
| | | | 35 | | | | | 40 | | | | | 45 | | |
| Leu | Ser | Tyr | His | Leu | Asp | Leu | Trp | Gly | Lys | Asp | Lys | Asn | Ala | Thr | Glu |

-continued

```
         50                          55                          60
Arg  Ala  Leu  Asp  Thr  Ala  His  Ala  Thr  Ala  Ala  Asp  Ala  Arg  Ala  Ala
 65                      70                      75                       80
Lys  Leu  Glu  Leu  Glu  Val  Asn  Val  Val  Arg  Ala  Tyr  Val  Gly  Met  Ser
                         85                      90                       95
Met  Asn  Tyr  Ala  Leu  Leu  Asp  Leu  Ala  His  Glu  Thr  Phe  Glu  Arg  Gln
                100                     105                     110
Arg  Ser  Leu  Ala  Asp  Leu  Ala  Arg  Lys  Arg  Leu  Gln  Ala  Gly  Leu  Gly
                115                     120                     125
Thr  Gln  Leu  Glu  Val  Ser  Gln  Ala  Glu  Ser  Thr  Leu  Pro  Asp  Tyr  Glu
           130                     135                     140
Arg  Gln  Ile  Asp  Ser  Tyr  Glu  Glu  Ala  Ile  Gln  Leu  Ala  Arg  His  Gln
145                     150                     155                      160
Leu  Ala  Ala  Leu  Ala  Gly  Lys  Gly  Pro  Gly  Ala  Gly  Asp  Ala  Ile  Lys
                     165                     170                     175
Arg  Pro  Arg  Leu  Ser  Leu  Asp  Ala  Pro  Ala  Gly  Leu  Pro  Ser  Ala  Met
                180                     185                     190
Pro  Ala  Asp  Leu  Leu  Gly  Arg  Arg  Pro  Asp  Val  Val  Ala  Ala  Arg  Trp
                195                     200                     205
Thr  Val  Asp  Ala  Gln  Ala  Arg  Gly  Ile  Asp  Val  Ala  Lys  Ala  Ser  Phe
           210                     215                     220
Tyr  Pro  Asn  Ile  Asp  Leu  Leu  Ala  Thr  Val  Gly  Gly  Phe  Gly  Val  Thr
225                     230                     235                      240
Ala  Pro  Phe  Thr  Asp  Phe  Leu  Arg  Ala  Met  Asn  Gly  Gly  Trp  Thr  Ala
                245                     250                     255
Gly  Pro  Ala  Leu  Ser  Leu  Pro  Ile  Phe  Glu  Gly  Gly  Arg  Leu  Arg  Ala
                260                     265                     270
Gln  Leu  Gly  Ala  Ala  Asn  Ala  Gly  Val  Arg  Pro  Gly  Gly  Arg  Ala  Ile
           275                     280                     285
Gln  Pro  Asp  Asp  Arg  Arg  Arg  Ala  Gln  Gly  His  Arg  Arg  Pro  Gly  Arg
      290                     295                     300
Ala  Asp  Pro  Phe  Ala  Arg  Tyr  Ala  Glu  Glu  Gly  Arg  Arg  Thr  Leu  Gly
305                     310                     315                      320
Gly  Arg  Gln  Arg  Pro  Gln  Leu  Pro  Ala  Val  Ala  Arg  Arg  Leu  Pro  Pro
                325                     330                     335
Arg  Pro  Asp  Arg  Leu  Arg  Gln  Arg  Ala  Gly  Arg  Ala  Ala  Ala  Ile  Val
           340                     345                     350
Gly  Ala  His  Arg  Lys  Arg  Pro  Pro  His  Arg  Ser  Glu  Arg  Leu  Ala  Ala
           355                     360                     365
His  Ala  Gln  Leu  Met  Ala  Ala  Leu  Gly  Gly  Gly  Val  Glu  Thr  Gly  Thr
     370                     375                     380
Asp  Val  Pro  Gly  Ser  Gln  Ser  Ser  His  Gly  Glu  Ser  Ala  Ala  Gly  Ala
385                     390                     395                      400
Ala  Ala  Pro  Ala  Ala  Ala  Ser  Gly  Ala  Lys  Pro  Val  Ala  Ala  Ala  Ala
                405                     410                     415
Arg  Pro  Ala  Gln  Val  Ala  Ala  Ala  Gly  Ala  Ala  Gly  Val  Pro  Ala  Ala
           420                     425                     430
Arg
```

(2) INFORMATION FOR SEQ ID NO:3:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met<br>1 | Ser | Ala | Ser | Ser<br>5 | Pro | Leu | Ser | Pro | Thr<br>10 | Ala | Gly | Gly | Pro | Phe<br>15 | Ala |
| Ala | Trp | Tyr | Ala<br>20 | Ala | Phe | Gly | Asp | Trp<br>25 | Ala | Arg | Thr | Asp | Gly<br>30 | Ala | Ala |
| Trp | Leu | Tyr<br>35 | Leu | Phe | Lys | Ala | Leu<br>40 | Leu | Ala | Ala | Phe | Ile<br>45 | Ala | Leu | Gly |
| Val | Ser<br>50 | Met | Arg | Leu | Asp | Leu<br>55 | Pro | Ala | Pro | Lys | Thr<br>60 | Ala | Met | Thr | Thr |
| Val<br>65 | Phe | Ile | Val | Met | Gln<br>70 | Arg | Lys | Ala | Ala | Pro<br>75 | Cys | Ser | Arg | Lys | Ala<br>80 |
| Ser | Thr | Gly | Ser | Pro<br>85 | Ala | Arg | Ser | Ser | Gly<br>90 | Ser | Ser | Arg | Arg | Ser<br>95 | Arg |
| Ser | Ser | Gly | Cys<br>100 | Ser | Arg | Ser | Ser | Arg<br>105 | Ser | Cys | Ser | Cys | Trp<br>110 | Arg | Ser |
| Pro | Cys | Gly<br>115 | Ser | Arg | Cys | Ala | Pro<br>120 | Pro | Ala | Pro | Arg | Ala<br>125 | Thr | Ala | Thr |
| Ser | Ala<br>130 | Val | Thr | Ala | Ser | Cys<br>135 | Ser | Pro | Ala | Ile | Arg<br>140 | Pro | Arg | | |

( 2 ) INFORMATION FOR SEQ ID NO:4:

( i ) SEQUENCE CHARACTERISTICS:
( A ) LENGTH: 346 amino acids
( B ) TYPE: amino acid
( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met<br>1 | Ser | Ala | Met | Thr<br>5 | Arg | Val | Ser | Glu | Val<br>10 | Ile | Ile | Gly | Ile | Val<br>15 | Ser |
| Ala | Gly | Val | Val<br>20 | Ser | Ala | Leu | Val | Phe<br>25 | Pro | Arg | Tyr | Thr | Gly<br>30 | Glu | Gln |
| Met | Arg | Thr<br>35 | Thr | Val | Arg | Lys | Arg<br>40 | Phe | Gly | Ser | Phe | Val<br>45 | Asp | Tyr | Val |
| Ala | Ser<br>50 | Ala | Leu | Ser | Gly | Gln<br>55 | Leu | Asp | Arg | Ala | His<br>60 | Ile | Glu | Thr | Ile |
| His<br>65 | Thr | Arg | Phe | Ala | Tyr<br>70 | Val | Val | Gly | Phe | Glu<br>75 | Ala | Ala | Arg | Ser | Met<br>80 |
| Ala | Val | Phe | Glu | Asp<br>85 | Pro | Asp | Thr | Arg | Met<br>90 | Arg | Ser | Gly | Arg | Leu<br>95 | Ala |
| Arg | Leu | Asn | Ser<br>100 | Glu | Phe | Met | Ser | Ala<br>105 | Ser | Ser | Arg | Phe | His<br>110 | Ala | Leu |
| His | Gln | Leu<br>115 | Met | Asn | Arg | Leu | His<br>120 | Ala | Ala | Gly | Ala | Gln<br>125 | Ala | Ala | Ile |
| Asp | Ala<br>130 | Ile | Glu | Pro | Tyr | Phe<br>135 | Arg | Glu | Ile | Ala | Pro<br>140 | Leu | Leu | Thr | Arg |
| Asn<br>145 | Gly | Glu | Pro | Val | Arg<br>150 | Thr | Ser | Ile | Asp | Ala<br>155 | Ala | His | Ser | Ala | Glu<br>160 |
| Gln | Leu | Leu | Ala | Trp<br>165 | Arg | Asp | Ala | Leu | Pro<br>170 | Arg | Arg | Ile | Arg | Ala<br>175 | Thr |
| Arg | Ala | Glu | Leu<br>180 | Glu | Thr | Gln | Pro | Asp<br>185 | Phe | Pro | Leu | Leu | Asp<br>190 | Phe | Asp |
| Thr | Ala | Ala | Glu<br>195 | Leu | Leu | Tyr | Arg<br>200 | Phe | Ile | Thr | Asp | Leu<br>205 | Gln | Glu | Tyr |
| Ala | Ala | Thr | Tyr | Ala | Ser | Leu | Ala | Thr | Ala | Thr | His | Glu | Arg | Glu | Arg |

-continued

```
         210                      215                      220
Trp Ile Glu Arg Tyr Glu Pro Arg Thr Asn Lys Thr Ala Ala Thr Ile
225                 230                 235                     240

Ala Gly Ile Arg Thr Ala Thr Val Ile Leu Ala Leu Gly Trp Phe Trp
                245                 250                 255

Ile Glu Thr Ala Trp Pro Ser Gly Val Met Leu Val Leu Asn Ala Ala
                260                 265                 270

Ala Thr Cys Ala Leu Ala Ser Ser Ala Pro Arg Pro Thr Ala Met Ala
            275                 280                 285

Ala Gln Met Gly Met Gly Thr Ala Leu Ala Val Cys Thr Gly Phe Leu
290                 295                 300

Leu Thr Phe Gly Ile Tyr Pro Arg Ile Asp Gly Phe Val Leu Leu Cys
305                 310                 315                     320

Ala Ala Leu Ala Pro Leu Leu Ala Ile Gly Ile Tyr Met Ser Leu Lys
                325                 330                 335

Pro Lys Leu Ala Gly Tyr Gly Gly Ala Ile
                340                 345
```

( 2 ) INFORMATION FOR SEQ ID NO:5:

( i ) SEQUENCE CHARACTERISTICS:
( A ) LENGTH: 208 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
Met Asn Asp Ala Leu Ala Leu Leu Leu Ser Met Leu Val Ser Ala Ile
1               5                   10                  15

Ala Phe Ala Val Leu Phe Pro Pro Thr Ala Pro Trp Leu Lys Lys Arg
            20                  25                  30

Leu Phe Ala Asp Leu Arg His Gln Ala Val Ala Ala Cys His Ala Arg
        35                  40                  45

Leu Ala Gly Leu Arg Thr Arg Phe Glu Ser Gly Ala Arg Asp Leu Met
50                  55                  60

Tyr Gln Ala His Thr Leu Ser Ala Asp His Pro Thr Cys Ser Ala Thr
65                  70                  75                      80

Pro Cys Trp Met Phe Ala Val Leu Glu Thr Gly Asn Ala Ala Ile Asp
                85                  90                      95

Leu Arg His Glu Leu Ala Thr Leu Pro Ser Asp Pro Arg Tyr Ala Pro
            100                 105                 110

Thr Thr Pro Trp Arg Arg Ala Ile Glu Thr Met Arg Ala Ala Leu Ser
            115                 120                 125

Ser Leu Phe Ala Arg Pro Asp Ala Glu Arg Phe Asp Ala Thr Leu Ala
130                 135                 140

Ala Val Asn Asp Ala Ile Asp Ala Thr Arg Gln Thr Leu Asp Ala Phe
145                 150                 155                     160

Thr Pro Thr Arg Glu Glu Arg His Arg Leu Gln Arg Ile Leu Ser His
                165                 170                 175

Leu His Phe Val Arg Thr Ala Leu Leu Asp Pro Glu Ser Pro Leu Ala
            180                 185                 190

Ala Leu Asn Arg Asn Arg Pro Val Arg Pro Gln Pro Gly Ala Ser Ser
        195                 200                 205
```

( 2 ) INFORMATION FOR SEQ ID NO:6:

( i ) SEQUENCE CHARACTERISTICS:
( A ) LENGTH: 168 amino acids (B) TYPE: amino acid
(D) TOPOLOGY: linear (ii) MOLECULE TYPE: protein (xi) SEQUENCE DESCRIPTION: SEQ ID NO:6:

```
Met Gln Ile Asp Pro Ser His Tyr Gln Ile Ala Val Glu Gln Ala Gln
 1               5                  10                  15
Ala Val Ala Ala Ala Ala Arg Ser Cys Arg Cys Arg Arg Arg Gly Arg
                20                  25                  30
Arg Ala Asp Leu Asp Ala Leu Val Val Ser Lys Glu Asn Arg Glu Asn
             35                  40                  45
Ala Ala His Ser Ala Ser Ser Ala Asp Ala Gln Tyr Gln Gln Ala Ile
         50                  55                  60
Ala Ala Leu Asp Ala Arg Ser Ser Thr Leu Glu Arg Ser Arg Val Val
 65                  70                  75                  80
Ala Pro Val Asp Gly Tyr Ile Thr Asn Leu Gln Thr Phe Lys Gly Asn
                 85                  90                  95
Tyr Ala Val Ala Gly Gln Ala Lys Leu Ala Ile Val Asp Ser His Ser
                100                 105                 110
Phe Trp Val Tyr Gly Tyr Phe Glu Glu Thr Lys Leu Pro Arg Val Lys
             115                 120                 125
Ile Gly Ala Pro Ala Glu Met Arg Leu Met Ser Gly Gly Val Met Lys
 130                 135                 140
Gly His Val Glu Ser Ile Ser Arg Gly Ile Tyr Asp Arg Asp Asn Pro
145                 150                 155                 160
Gln Ser Arg Asp Leu Val Arg Thr
                165
```

(2) INFORMATION FOR SEQ ID NO:7:

(i) SEQUENCE CHARACTERISTICS:
(A) LENGTH: 3606 base pairs
(B) TYPE: nucleic acid
(C) STRANDEDNESS: unknown
(D) TOPOLOGY: unknown (ii) MOLECULE TYPE: DNA (genomic)

(ix) FEATURE:
(A) NAME/KEY: CDS
(B) LOCATION: 385..813

(ix) FEATURE:
(A) NAME/KEY: CDS
(B) LOCATION: 1382..2083

(ix) FEATURE:
(A) NAME/KEY: CDS
(B) LOCATION: 2591..3011

(xi) SEQUENCE DESCRIPTION: SEQ ID NO:7:

```
GGATCCACAC CGCGCAGTCT GGCGGCACTA TCCAGATATC GTTTTCCGCA CGACAAATCA      60
CCGCCCCATA GAGGGCAACG ATCAGTTGTC CCTTGCGGTG GGTATGAACC GGCACTTCTG     120
CCGCGTAAAC AACGAAATCA ATATGCCGCG CGACGGCAGG GCTCGGCGTG CTATCGGCAT     180
CAAACAGGGT ATGGGCAAGT CTGGATGGCA TCTCATTGGC AACATTTAGG TATTTTTTGA     240
CAGAATAGAG TATTTAAGGA GACGCGCAAA GCGGAATAAT TCCCGGCATG AGCACATTAA     300
CTTCCCATCA CAGCCGTTTT TTACACGCGA TAAGCCGTTG GTCAGGGCCG CATAGCCTCT     360
CCCTGCGCTG CTTGAGCGAC GCCC ATG CCC TGC TCT ATT CCG TCA GGA GTT       411
                           Met Pro Cys Ser Ile Pro Ser Gly Val
                            1               5
```

| | | | | | | | | | | | | | | | | |
|---|---|---|---|---|---|---|---|---|---|---|---|---|---|---|---|---|
| TTG | CCG | CCG | CGA | TGC | TCG | CCT | ATT | ACG | TTG | CCC | TGG | CGA | TTG | GCC | TTG | 459 |
| Leu | Pro | Pro | Arg | Cys | Ser | Pro | Ile | Thr | Leu | Pro | Trp | Arg | Leu | Ala | Leu | |
| 10 | | | | 15 | | | | | 20 | | | | | | 25 | |
| AAC | GCC | CTC | ATG | GGC | ACT | CAT | CAC | CGT | CTA | CAT | CGT | GTC | GCA | AAC | CTC | 507 |
| Asn | Ala | Leu | Met | Gly | Thr | His | His | Arg | Leu | His | Arg | Val | Ala | Asn | Leu | |
| | | | 30 | | | | | 35 | | | | | 40 | | | |
| GGT | GGG | CGC | TCC | CTG | TGC | AGA | AGC | CTT | TAT | CGC | CTG | GCC | GGT | ACC | GTG | 555 |
| Gly | Gly | Arg | Ser | Leu | Cys | Arg | Ser | Leu | Tyr | Arg | Leu | Ala | Gly | Thr | Val | |
| | | | 45 | | | | | 50 | | | | | 55 | | | |
| GCC | GGC | GCG | GGG | GCC | ACG | GTA | TTG | ATT | GTG | CCG | ACG | TTT | GTG | AAT | ACG | 603 |
| Ala | Gly | Ala | Gly | Ala | Thr | Val | Leu | Ile | Val | Pro | Thr | Phe | Val | Asn | Thr | |
| | | 60 | | | | | 65 | | | | | 70 | | | | |
| CCA | ATT | CTA | TGT | AGC | GTG | ATT | CTG | GCT | GGC | TGG | ATC | ACC | TTC | TGC | CTC | 651 |
| Pro | Ile | Leu | Cys | Ser | Val | Ile | Leu | Ala | Gly | Trp | Ile | Thr | Phe | Cys | Leu | |
| | | 75 | | | | | 80 | | | | | 85 | | | | |
| TAT | TTA | TCC | CTG | CTT | GAA | CGC | ACG | CCC | CGC | GCC | TAT | GCC | TTT | GTG | CTG | 699 |
| Tyr | Leu | Ser | Leu | Leu | Glu | Arg | Thr | Pro | Arg | Ala | Tyr | Ala | Phe | Val | Leu | |
| 90 | | | | | 95 | | | | | 100 | | | | | 105 | |
| GCC | GGT | TAT | ACC | GCA | AGC | CTG | ATT | GGT | TTT | CCC | GCC | GTC | GCC | GAT | CCC | 747 |
| Ala | Gly | Tyr | Thr | Ala | Ser | Leu | Ile | Gly | Phe | Pro | Ala | Val | Ala | Asp | Pro | |
| | | | 110 | | | | | 115 | | | | | 120 | | | |
| GGC | ACG | TGT | TTA | ACA | TCG | CCC | TCA | TCC | GGG | TAC | AGG | AAA | TCG | CGA | TCG | 795 |
| Gly | Thr | Cys | Leu | Thr | Ser | Pro | Ser | Ser | Gly | Tyr | Arg | Lys | Ser | Arg | Ser | |
| | | | 125 | | | | | 130 | | | | | 135 | | | |
| GTA | TCG | TCT | GCG | CCG | CGC | TGATTCACCG | CTACATTTTA | CCTGCCCGGA | | | | | | | | 843 |
| Val | Ser | Ser | Ala | Pro | Arg | | | | | | | | | | | |
| | | | 140 | | | | | | | | | | | | | |

| | | | |
|---|---|---|---|
| TATCAGGGCT | GTTCAACAGC | AAATTAGCCC | AGACGCTGCA CGCCGCGCGC CAGGATTGCC | 903 |
| GACACCCTGG | CAGGCAAGGC | CGACGCGCAG | TCTGAGCCGC TGCATCTGGC GCTGGCGCTA | 963 |
| CAGTTTCTTC | AGGGCATCAG | CCACCATATC | CCGTATGATT TTGCCCTTTC GGTTCCGGCC | 1023 |
| CGCCAGGCCA | GGAAAGCGCT | CCATGACAGG | CTGGCGCGGT TAGTGATTGT CAACGGCGAA | 1083 |
| GTGCGCGATC | GTTTGCAGAT | CATCGCCGGG | ATGCCGCCG CGATGCAGAC TCTACTGAAT | 1143 |
| GACGTGCAGG | CCTGGCTGAC | CTGCGACGAT | ACCGGCCAAC GCAAAAACGC CGCAGAAGCG | 1203 |
| CTGCAACAGC | GCAGCGCAGT | TAGCGCGGCG | GCTCGCGGCG CAGGCGCTGA CCTTTGAAGA | 1263 |
| TGCGCTGCGG | GTAAATTTCT | TACGCTACAT | CGCTGAGTTG ATTACCCTCC TGCAGCAGTG | 1323 |
| TGAGCGGCTT | TCGGAGGCCA | TTCATCACGC | CAGACCTGCG CCAGCGCATG GAAGAATC | 1381 |

| | | | | | | | | | | | | | | | | |
|---|---|---|---|---|---|---|---|---|---|---|---|---|---|---|---|---|
| GTG | CGG | CGA | CAG | GAT | ACG | TTT | TCC | ATC | GCG | ATC | CCC | TCC | AGC | GCC | GCC | 1429 |
| Val | Arg | Arg | Gln | Asp | Thr | Phe | Ser | Ile | Ala | Ile | Pro | Ser | Ser | Ala | Ala | |
| 1 | | | | 5 | | | | | 10 | | | | | 15 | | |
| CGC | ACG | GCG | CTG | GGC | GCT | TTT | GTC | ATC | ATT | CTG | AGC | GGC | TGT | CTG | CTA | 1477 |
| Arg | Thr | Ala | Leu | Gly | Ala | Phe | Val | Ile | Ile | Leu | Ser | Gly | Cys | Leu | Leu | |
| | | | 20 | | | | | 25 | | | | | 30 | | | |
| TGG | ATT | TAC | TCT | GCC | TGG | CCC | GAT | GGC | GGC | ACG | GCG | GTG | TCG | ATT | CTC | 1525 |
| Trp | Ile | Tyr | Ser | Ala | Trp | Pro | Asp | Gly | Gly | Thr | Ala | Val | Ser | Ile | Leu | |
| | | 35 | | | | | 40 | | | | | 45 | | | | |
| GGG | GTT | TGC | TGC | ACG | CTG | TTT | GGC | AGT | TTC | GAC | ACG | CCG | GCC | CCG | CAT | 1573 |
| Gly | Val | Cys | Cys | Thr | Leu | Phe | Gly | Ser | Phe | Asp | Thr | Pro | Ala | Pro | His | |
| | 50 | | | | | 55 | | | | | 60 | | | | | |
| ATT | GTG | AAA | TAT | ATT | ATC | GGC | TCT | GTC | TGG | GGC | GTA | GTG | ATA | AGC | CTT | 1621 |
| Ile | Val | Lys | Tyr | Ile | Ile | Gly | Ser | Val | Trp | Gly | Val | Val | Ile | Ser | Leu | |
| 65 | | | | 70 | | | | | 75 | | | | | | 80 | |
| ATC | TAT | AGC | TTC | GCC | CTG | CTT | CCT | CCG | CTC | AGC | GAT | TTC | CCC | GTG | CTG | 1669 |
| Ile | Tyr | Ser | Phe | Ala | Leu | Leu | Pro | Pro | Leu | Ser | Asp | Phe | Pro | Val | Leu | |
| | | | 85 | | | | | 90 | | | | | 95 | | | |
| GTG | GCG | GTG | CTT | GCC | CCG | GTC | TAT | CTG | CTT | GCC | GGA | TCG | CTG | CAG | GCG | 1717 |
| Val | Ala | Val | Leu | Ala | Pro | Val | Tyr | Leu | Leu | Ala | Gly | Ser | Leu | Gln | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| CGG | CCC | CCC | ACG | ACC | TTT | ATG | GCC | ATG | GGC | ATC | ACC | CTG | ACG | CTG | CCG | 1765 |
| Arg | Pro | Pro | Thr | Thr | Phe | Met | Ala | Met | Gly | Ile | Thr | Leu | Thr | Leu | Pro | |
| | | 115 | | | | | 120 | | | | | 125 | | | | |
| GTA | CTG | TGC | GAG | CTG | GGC | GCG | CGC | TAC | AGC | GGC | GAC | TTC | GCC | GAC | GCG | 1813 |
| Val | Leu | Cys | Glu | Leu | Gly | Ala | Arg | Tyr | Ser | Gly | Asp | Phe | Ala | Asp | Ala | |
| 130 | | | | | 135 | | | | | 140 | | | | | | |
| GCC | AAC | ACC | GCG | ATC | GCC | CTG | TTT | TTC | GCG | ACC | GGC | TTT | GCG | GTT | ATC | 1861 |
| Ala | Asn | Thr | Ala | Ile | Ala | Leu | Phe | Phe | Ala | Thr | Gly | Phe | Ala | Val | Ile | |
| 145 | | | | | 150 | | | | | 155 | | | | | 160 | |
| GGC | ATG | AGT | CTG | CTG | CAA | ACC | GTA | CAG | GCG | GAC | GCG | GCG | ATA | AAG | CGT | 1909 |
| Gly | Met | Ser | Leu | Leu | Gln | Thr | Val | Gln | Ala | Asp | Ala | Ala | Ile | Lys | Arg | |
| | | | | 165 | | | | | 170 | | | | | 175 | | |
| CTG | CTG | AAA | CTG | TGC | CAA | CGC | GAT | ATT | CGC | CGC | AGC | GTG | AGC | GGC | GTA | 1957 |
| Leu | Leu | Lys | Leu | Cys | Gln | Arg | Asp | Ile | Arg | Arg | Ser | Val | Ser | Gly | Val | |
| | | | 180 | | | | | 185 | | | | | 190 | | | |
| TTT | AAA | GGC | GAT | GAA | ACG | CAC | TGG | ACC | AAT | CTG | ATG | ATC | GAC | CGG | GGC | 2005 |
| Phe | Lys | Gly | Asp | Glu | Thr | His | Trp | Thr | Asn | Leu | Met | Ile | Asp | Arg | Gly | |
| | | | 195 | | | | | 200 | | | | | 205 | | | |
| CGT | CTG | CTG | CTG | CCA | CGC | TTG | CGC | GCA | GCG | GGC | AGT | CCT | CCG | CCC | GGG | 2053 |
| Arg | Leu | Leu | Leu | Pro | Arg | Leu | Arg | Ala | Ala | Gly | Ser | Pro | Pro | Pro | Gly | |
| | | 210 | | | | | 215 | | | | | 220 | | | | |
| CGC | TCG | ATC | GCC | TGG | TGC | ACT | TTC | TGC | GCA | TAGGCCTCTG CGTTATGCGC | | | | | | 2103 |
| Arg | Ser | Ile | Ala | Trp | Cys | Thr | Phe | Cys | Ala | | | | | | | |
| 225 | | | | | 230 | | | | | | | | | | | |

| | |
|---|---|
| CTGCGCCGTT GCGAAACGCC CGCCGGCAGC GATATCCACG AGGTGCTTTC TCGTCTTACC | 2163 |
| CACACAACGG AGACCGAAGC CTTACGCGAG CGCATTGCCG CCATGGCGAA CCGCTGCTTG | 2223 |
| CCCGCGAGGG AGGAACAATC ATGCCAGTTT GTCGACCGAC TGGTCGATCT GCACTGCGCG | 2283 |
| TTACGGACGC AGAACGAGGA ACCCACCCAT GATAAATGAC ATCAATATCG GGGCGTTTT | 2343 |
| TATCCCCGGA CTGCTGCTGA CCGCGCTCAT TGCCCTGGTC TGTACGCTGT TACTCGTACC | 2403 |
| GCTTTTCTCT GCAGCAGGCT TTACCGCCGC TTGCCCTTAC GCCCGCTGCT TGATGTTTCA | 2463 |
| ACCTATATCG TGACCTTTTT CCTGCTTTTG CAGGGCCTGA CCACACTGGG GTTATTCGCA | 2523 |
| TGAAATCTTT TTTCTCTTTG CTGGGCCGTT ACGCGCTGAC GTTAATCGCA GTAGCGGTAG | 2583 |

| | | | | | | | | | | | | | | | | |
|---|---|---|---|---|---|---|---|---|---|---|---|---|---|---|---|---|
| CGCCTGC | GTG | GCG | TTT | ATT | TTC | TGG | AAA | CAG | TAT | GCG | CAG | ACG | CCC | TGG | | 2632 |
| | Val | Ala | Phe | Ile | Phe | Trp | Lys | Gln | Tyr | Ala | Gln | Thr | Pro | Trp | | |
| | 1 | | | | 5 | | | | | 10 | | | | | | |
| ACG | CGC | GAT | GGC | CGG | GTT | CGG | GCA | GAT | GTG | GTG | CAG | ATT | GCG | CCG | GAT | 2680 |
| Thr | Arg | Asp | Gly | Arg | Val | Arg | Ala | Asp | Val | Val | Gln | Ile | Ala | Pro | Asp | |
| 15 | | | | | 20 | | | | | 25 | | | | | 30 | |
| GTT | TCC | GGG | CCG | GTG | AGC | AGC | GTG | GCG | GTG | CGG | GAT | AAT | CAG | TGG | GTT | 2728 |
| Val | Ser | Gly | Pro | Val | Ser | Ser | Val | Ala | Val | Arg | Asp | Asn | Gln | Trp | Val | |
| | | | | 35 | | | | | 40 | | | | | 45 | | |
| AAC | CGC | GGC | GAT | GTG | CTT | TAT | CGG | ATC | GAC | CCG | CGC | TGG | CTG | AAG | CTG | 2776 |
| Asn | Arg | Gly | Asp | Val | Leu | Tyr | Arg | Ile | Asp | Pro | Arg | Trp | Leu | Lys | Leu | |
| | | | 50 | | | | | 55 | | | | | 60 | | | |
| GCG | GTG | CTC | AGC | GCG | CAG | GCC | GAC | GTC | GAA | GCA | AAA | CGT | CAT | GAA | ATG | 2824 |
| Ala | Val | Leu | Ser | Ala | Gln | Ala | Asp | Val | Glu | Ala | Lys | Arg | His | Glu | Met | |
| | 65 | | | | | 70 | | | | | 75 | | | | | |
| CTG | ATG | CGC | CAG | GAT | GCC | GCC | CCG | CCA | CGC | GCG | CTC | ATC | AAA | GGG | GTC | 2872 |
| Leu | Met | Arg | Gln | Asp | Ala | Ala | Pro | Pro | Arg | Ala | Leu | Ile | Lys | Gly | Val | |
| | 80 | | | | | 85 | | | | | 90 | | | | | |
| ATT | TCC | GGC | GAG | GAT | ATC | CAG | CAA | ACA | GGC | AGC | GCA | GCT | GCT | GTT | CGC | 2920 |
| Ile | Ser | Gly | Glu | Asp | Ile | Gln | Gln | Thr | Gly | Ser | Ala | Ala | Ala | Val | Arg | |
| 95 | | | | | 100 | | | | | 105 | | | | | 110 | |
| GGC | GGC | CAA | TTA | TCA | GGG | GGC | GCT | GGC | TGC | GCT | GGA | ACT | GGC | GCA | GTG | 2968 |
| Gly | Gly | Gln | Leu | Ser | Gly | Gly | Ala | Gly | Cys | Ala | Gly | Thr | Gly | Ala | Val | |
| | | | | 115 | | | | | 120 | | | | | 125 | | |
| AAA | CTT | ATC | CCA | TGC | AAC | GCT | ACG | CCC | CCG | TTA | CCG | CGT | ACGTGACGCA | | | 3017 |

```
Lys Leu Ile Pro Cys Asn Ala Thr Pro Pro Leu Pro Arg Thr
            130                 135             140
```

| | |
|---|---|
| TCTTCGGCTC CGCCCGGCGA CTACGCCGCG GCGGGAGAAA CAAAGGTCGC CGTGGTCGAT | 3077 |
| GCGCACAGTT TCTGGGTGGT GGGCTATTTT GAGAGGACAA GCTGCGTCAT ATTCGCGTCG | 3137 |
| GGAGCGCCGC ACACATTTCT CTGATGGGGT TTGACCCGCT CATCACCGGG CACGTGGAGA | 3197 |
| GTATCGGCCG GGGGATCGAT GATAGCAATG ACGAGACCGG CGGGCTGGGG CTGCCGGATG | 3257 |
| TCAATCCCAC CTTCAGCTGG GTGCGACTTG CGCAGCGAGT CCCCGTTCGT ATACAGTTAG | 3317 |
| ATAAGATACC GGAAGGGATT GAACTGGTGG CGGGACTATC CGCCAGCGTT CCATCCTGC | 3377 |
| CTGAAAGCCT AGACGGCGGG CGTAGCGGAG GATCGGGCTA CGTGGCTCAG GCTATCCACC | 3437 |
| CATAGTGGAC CCGAGACTCA ATGAGGAAAC GACGCTTCTG CAAAAATATC TGGCCCGAAT | 3497 |
| ATACCGAACT CGATATTCTG TAATGCTTTG TATTTTTTGT GAACAGGAAA AAGTATGCTT | 3557 |
| AGTACGTTAC CCGATTTACA CAGAAGTTTT GCAGAGCAAC TCAAGTATT | 3606 |

(2) INFORMATION FOR SEQ ID NO:8:

(i) SEQUENCE CHARACTERISTICS:
        (A) LENGTH: 143 amino acids
        (B) TYPE: amino acid
        (D) TOPOLOGY: linear (ii) MOLECULE TYPE: protein (xi) SEQUENCE DESCRIPTION: SEQ ID NO:8:

```
Met Pro Cys Ser Ile Pro Ser Gly Val Leu Pro Pro Arg Cys Ser Pro
 1               5                  10                  15
Ile Thr Leu Pro Trp Arg Leu Ala Leu Asn Ala Leu Met Gly Thr His
                20                  25                  30
His Arg Leu His Arg Val Ala Asn Leu Gly Gly Arg Ser Leu Cys Arg
            35                  40                  45
Ser Leu Tyr Arg Leu Ala Gly Thr Val Ala Gly Ala Gly Ala Thr Val
        50                  55                  60
Leu Ile Val Pro Thr Phe Val Asn Thr Pro Ile Leu Cys Ser Val Ile
 65                  70                  75                  80
Leu Ala Gly Trp Ile Thr Phe Cys Leu Tyr Leu Ser Leu Leu Glu Arg
                85                  90                  95
Thr Pro Arg Ala Tyr Ala Phe Val Leu Ala Gly Tyr Thr Ala Ser Leu
                100                 105                 110
Ile Gly Phe Pro Ala Val Ala Asp Pro Gly Thr Cys Leu Thr Ser Pro
            115                 120                 125
Ser Ser Gly Tyr Arg Lys Ser Arg Ser Val Ser Ser Ala Pro Arg
        130                 135                 140
```

(2) INFORMATION FOR SEQ ID NO:9:

(i) SEQUENCE CHARACTERISTICS:
        (A) LENGTH: 234 amino acids
        (B) TYPE: amino acid
        (D) TOPOLOGY: linear (ii) MOLECULE TYPE: protein (xi) SEQUENCE DESCRIPTION: SEQ ID NO:9:

```
Val Arg Arg Gln Asp Thr Phe Ser Ile Ala Ile Pro Ser Ser Ala Ala
 1               5                  10                  15
Arg Thr Ala Leu Gly Ala Phe Val Ile Ile Leu Ser Gly Cys Leu Leu
                20                  25                  30
Trp Ile Tyr Ser Ala Trp Pro Asp Gly Gly Thr Ala Val Ser Ile Leu
            35                  40                  45
```

```
Gly Val Cys Cys Thr Leu Phe Gly Ser Phe Asp Thr Pro Ala Pro His
    50                  55                  60

Ile Val Lys Tyr Ile Ile Gly Ser Val Trp Gly Val Val Ile Ser Leu
65                  70                  75                      80

Ile Tyr Ser Phe Ala Leu Leu Pro Pro Leu Ser Asp Phe Pro Val Leu
                85                  90                  95

Val Ala Val Leu Ala Pro Val Tyr Leu Leu Ala Gly Ser Leu Gln Ala
            100                 105                 110

Arg Pro Pro Thr Thr Phe Met Ala Met Gly Ile Thr Leu Thr Leu Pro
        115                 120                 125

Val Leu Cys Glu Leu Gly Ala Arg Tyr Ser Gly Asp Phe Ala Asp Ala
    130                 135                 140

Ala Asn Thr Ala Ile Ala Leu Phe Phe Ala Thr Gly Phe Ala Val Ile
145                 150                 155                 160

Gly Met Ser Leu Leu Gln Thr Val Gln Ala Asp Ala Ala Ile Lys Arg
                165                 170                 175

Leu Leu Lys Leu Cys Gln Arg Asp Ile Arg Arg Ser Val Ser Gly Val
            180                 185                 190

Phe Lys Gly Asp Glu Thr His Trp Thr Asn Leu Met Ile Asp Arg Gly
        195                 200                 205

Arg Leu Leu Leu Pro Arg Leu Arg Ala Ala Gly Ser Pro Pro Pro Gly
    210                 215                 220

Arg Ser Ile Ala Trp Cys Thr Phe Cys Ala
225                 230
```

( 2 ) INFORMATION FOR SEQ ID NO:10:

( i ) SEQUENCE CHARACTERISTICS:
        ( A ) LENGTH: 140 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Val Ala Phe Ile Phe Trp Lys Gln Tyr Ala Gln Thr Pro Trp Thr Arg
1               5                   10                  15

Asp Gly Arg Val Arg Ala Asp Val Val Gln Ile Ala Pro Asp Val Ser
            20                  25                  30

Gly Pro Val Ser Ser Val Ala Val Arg Asp Asn Gln Trp Val Asn Arg
        35                  40                  45

Gly Asp Val Leu Tyr Arg Ile Asp Pro Arg Trp Leu Lys Leu Ala Val
    50                  55                  60

Leu Ser Ala Gln Ala Asp Val Glu Ala Lys Arg His Glu Met Leu Met
65                  70                  75                      80

Arg Gln Asp Ala Ala Pro Pro Arg Ala Leu Ile Lys Gly Val Ile Ser
                85                  90                  95

Gly Glu Asp Ile Gln Gln Thr Gly Ser Ala Ala Ala Val Arg Gly Gly
            100                 105                 110

Gln Leu Ser Gly Gly Ala Gly Cys Ala Gly Thr Gly Ala Val Lys Leu
        115                 120                 125

Ile Pro Cys Asn Ala Thr Pro Pro Leu Pro Arg Thr
    130                 135                 140
```

( 2 ) INFORMATION FOR SEQ ID NO:11:

( i ) SEQUENCE CHARACTERISTICS:
        ( A ) LENGTH: 1299 base pairs
        ( B ) TYPE: nucleic acid (C) STRANDEDNESS: unknown
(D) TOPOLOGY: unknown (ii) MOLECULE TYPE: DNA (genomic)

(vi) ORIGINAL SOURCE:
(A) ORGANISM: Pseudomonas cepacia (xi) SEQUENCE DESCRIPTION: SEQ ID NO:11:

| | | | | | | |
|---|---|---|---|---|---|---|
| ATGGCGCGCG | TGGCCCGCTC | GGCCGAATTG | CCACAGATCA | ACGGCAACCT | CTCGCTGATG | 60 |
| CGCCAGCACT | GGCCGGACAA | CGTCTATTAC | GGCCCCGGCC | CGCTCGCGAA | CACCGACACC | 120 |
| TGGAACAACA | CCGGCACGCT | CGGCCTGTCC | TACCACCTCG | ACCTGTGGGG | CAAGGACAAG | 180 |
| AACGCGACCG | AGCGCGCGCT | CGATACCGCG | CACGCGACCG | CCGCCGACGC | ACGCGCGGCG | 240 |
| AAGCTCGAAC | TCGAAGTCAA | CGTCGTGCGC | GCGTACGTCG | GCATGTCGAT | GAACTACGCG | 300 |
| CTGCTCGACC | TCGCGCACGA | AACGTTCGAA | CGCCAGCGCT | CGCTCGCCGA | TCTCGCGCGC | 360 |
| AAGCGGCTGC | AGGCTGGCCT | CGGCACGCAG | CTCGAGGTGA | GCCAGGCGGA | ATCGACGCTG | 420 |
| CCCGACTATG | AGCGCCAGAT | CGACAGCTAC | GAGGAAGCGA | TCCAGCTCGC | GCGGCACCAG | 480 |
| CTCGCCGCAC | TGGCCGGCAA | GGGCCCGGGC | GCCGGCGATG | CGATCAAGCG | GCCTCGGCTG | 540 |
| TCGCTCGACG | CACCGGCCGG | CTTGCCGTCG | GCGATGCCGG | CCGACCTGCT | CGGCCGCCGC | 600 |
| CCCGACGTCG | TCGCGGCACG | CTGGACGGTC | GACGCGCAGG | CGCGCGGCAT | CGACGTCGCA | 660 |
| AAGGCTTCGT | TCTATCCGAA | CATCGACCTG | CTCGCGACGG | TCGGCGGCTT | CGGCGTGACC | 720 |
| GCGCCGTTCA | CCGACTTCCT | GCGCGCGATG | AACGGCGGCT | GGACGGCCGG | CCCCGCGCTG | 780 |
| TCGCTGCCGA | TCTTCGAAGG | CGGCCGGCTG | CGCGCGCAGC | TCGGCGCGGC | GAATGCCGGC | 840 |
| GTACGACCAG | GCGGTCGAGC | AATACAACCA | GACGATCGTC | GGCGCGCTCA | AGGACATCGC | 900 |
| CGACCAGGTC | GTGCGGATCC | GTTCGCTCGA | TACGCAGAAG | AAGGACGCCG | CACGCTCGGT | 960 |
| GGCCGCCAAC | GACCGCAGTT | ACCAGCTGTC | GCGCGAAGGC | TTCCGCCGCG | GCCTGACCGA | 1020 |
| CTACGTCAAC | GTGCTGGTCG | CGCAGCAGCA | ATTGTTGGCG | CGCACAGGAA | ACGGCCGCCG | 1080 |
| CATCGATCGG | AACGCCTCGC | CGCGCACGCT | CAACTGATGG | CCGCGCTGGG | TGGCGGCGTC | 1140 |
| GAGACGGGCA | CGGACGTGCC | GGGCAGCCAA | TCGTCGCATG | GCGAATCCGC | CGCGGGCGCA | 1200 |
| GCCGCGCCGG | CCGCCGCGTC | GGGTGCGAAA | CCCGTGGCAG | CCGCCGCCCG | GCCCGCGCAG | 1260 |
| GTCGCGGCCG | CCGGTGCCGC | CGGCGTGCCG | GCCGCACGG | | | 1299 |

(2) INFORMATION FOR SEQ ID NO:12:

(i) SEQUENCE CHARACTERISTICS:
(A) LENGTH: 426 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:12:

| | | | | | | |
|---|---|---|---|---|---|---|
| ATGTCAGCCT | CCTCCCCCCT | CTCCCCGACC | GCCGGCGGTC | CGTTCGCGGC | CTGGTATGCC | 60 |
| GCGTTCGGCG | ACTGGGCCCG | CACCGACGGC | GCCGCGTGGC | TCTACCTGTT | CAAGGCACTG | 120 |
| CTCGCGGCCT | TCATCGCGCT | CGGCGTGTCG | ATGCGGCTCG | ACCTGCCGGC | GCCGAAAACG | 180 |
| GCAATGACGA | CCGTCTTCAT | CGTGATGCAG | CGCAAAGCGG | CGCCGTGCTC | GCGAAAAGCT | 240 |
| TCTACCGGGT | CGCCGGCACG | ATCTTCGGGC | TCATCGCGAC | GCTCACGTTC | GTCGGGCTGT | 300 |
| TCCCGCAGCA | GCCGCAGCTG | TTCCTGCTGG | CGATCGCCCT | GTGGATCGCG | CTGTGCACCG | 360 |
| CCGGCGCCGC | GCGCAACCGC | AACTTCCGCA | GTTACGGCTT | CCTGCTCGCC | GGCTATACGA | 420 |
| CCGCGC | | | | | | 426 |

(2) INFORMATION FOR SEQ ID NO:13:

(i) SEQUENCE CHARACTERISTICS:
        (A) LENGTH: 1038 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:13:

```
ATGAGCGCGA TGACGCGGGT CTCCGAAGTC ATCATCGGGA TCGTGTCGGC CGGCGTCGTC      60
AGCGCGCTCG TGTTTCCTCG GTACACGGGC GAGCAGATGC GCACGACGGT GCGCAAGCGC     120
TTCGGCAGCT TCGTCGACTA CGTCGCGTCG GCGCTGTCGG GCCAGCTCGA CCGCGCGCAC     180
ATCGAGACCA TCCATACGCG CTTCGCCTAC GTGGTCGGCT TCGAGGCCGC GCGCAGCATG     240
GCCGTGTTCG AGGATCCGGA CACGCGCATG CGCAGCGGCC GCCTCGCGCG GCTGAACAGC     300
GAGTTCATGA GCGCGTCGAG CCGCTTTCAC GCGCTGCACC AGCTGATGAA CCGGCTGCAC     360
GCGGCCGGCG CGCAGGCCGC GATCGATGCG ATCGAGCCGT ATTTCCGCGA GATCGCGCCG     420
CTGCTCACGC GCAATGGCGA ACCCGTGCGC ACGTCGATCG ACGCCGCGCA CTCGGCCGAG     480
CAACTGCTCG CGTGGCGCGA CGCGCTGCCG CGCCGTATCC GCGCGACACG CGCGGAACTC     540
GAAACGCAGC CCGACTTCCC GCTGCTCGAC TTCGATACCG CCGCCGAACT GCTGTACCGC     600
TTCATCACCG ACCTGCAGGA ATACGCGGCG ACCTATGCGT CGCTCGCGAC CGCGACGCAC     660
GAGCGCGAAC GCTGGATCGA ACGCTACGAG CCGCGCACCA ACAAAACGGC CGCCACGATC     720
GCGGGGATCC GCACCGCGAC GGTGATTCTC GCGCTCGGCT GGTTCTGGAT CGAGACTGCG     780
TGGCCGAGCG GCGTGATGCT GGTGCTGAAC GCCGCGGCGA CCTGCGCGCT CGCGTCGTCG     840
GCGCCGCGCC CGACCGCGAT GGCCGCGCAG ATGGGGATGG CACGGCGCT GGCCGTCTGC      900
ACCGGCTTCC TGCTGACGTT CGGCATCTAC CCGCGGATCG ACGGCTTCGT CCTGCTGTGC     960
GCGGCGCTCG CGCCGTTGCT CGCGATCGGC ATCTACATGT CGCTGAAGCC GAAGCTCGCC    1020
GGCTACGGCG GGGCTATC                                                  1038
```

(2) INFORMATION FOR SEQ ID NO:14:

(i) SEQUENCE CHARACTERISTICS:
        (A) LENGTH: 624 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:14:

```
ATGAACGACG CGCTCGCGCT CCTGTTGTCG ATGCTCGTCT CGGCTATCGC GTTCGCCGTG      60
CTGTTCCCGC CGACCGCGCC GTGGCTCAAG AAACGCCTGT CGCCGACCT GCGTCACCAG     120
GCCGTCGCGG CCTGCCACGC GCGGCTCGCC GGACTGCGCA CGCGCTTCGA GAGCGGCGCG     180
CGCGACCTGA TGTACCAGGC GCACACGCTG TCGGCCGACC ACCCGACGTG CAGCGCGACG     240
CCGTGCTGGA TGTTCGCGGT GCTCGAAACC GGGAATGCGG CCATCGACCT GCGCCACGAG     300
CTGGCAACGC TGCCGTCCGA CCCGCGCTAC GCGCCGACGA CGCCGTGGCG CCGTGCGATC     360
GAAACGATGC GCGCCGCGCT GTCGTCGCTG TTCGCGCGGC CGGACGCCGA ACGTTTCGAT     420
GCAACGCTCG CCGCGGTAAA CGATGCGATC GACGCGACCC GGCAGACGCT CGACGCATTC     480
ACGCCGACGC GCGAGGAACG CCACCGGCTG CAGCGCATCC TGAGCCATCT GCATTTCGTG     540
CGCACGGCAC TGCTCGATCC CGAATCGCCG CTCGCCGCGC TCAACCGCAA CCGCCCCGTG     600
```

```
CGTCCCCAAC CAGGAGCCTC GTCA                                                    624
```

(2) INFORMATION FOR SEQ ID NO:15:

(i) SEQUENCE CHARACTERISTICS:
        (A) LENGTH: 504 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:15:

```
ATGCAGATCG ACCCGTCGCA CTACCAGATC GCGGTCGAGC AGGCACAGGC CGTCGCCGCC    60
GCCGCGCGGA GCTGCAGATG CCGACGACGC GGCCGCCGCG CGGATCTCGA TGCGCTCGTC   120
GTGTCGAAGG AAAACCGCGA GAACGCCGCG CACAGTGCGT CGAGCGCCGA TGCACAGTAC   180
CAGCAGGCGA TCGCCGCGCT CGATGCGCGA AGCTCAACGC TCGAGCGCAG CCGCGTCGTC   240
GCGCCGGTCG ACGGCTACAT CACGAACCTG CAGACGTTCA AGGGCAACTA TGCGGTGGCC   300
GGCCAGGCGA AGCTCGCGAT CGTCGACAGC CACTCGTTCT GGGTCTACGG CTACTTCGAG   360
GAAACCAAGC TGCCGCGCGT GAAGATCGGC GCGCCGGCCG AAATGCGGCT GATGAGCGGC   420
GGCGTGATGA AGGGCCATGT CGAAAGCATC TCGCGCGGCA TCTACGATCG CGACAACCCG   480
CAAAGCCGCG ACCTCGTCCG GACG                                          504
```